(12) United States Patent
Singh et al.

(10) Patent No.: US 7,740,859 B2
(45) Date of Patent: Jun. 22, 2010

(54) POLYPEPTIDES FOR THE DIAGNOSIS AND THERAPY OF LEISHAMANIASIS

(75) Inventors: Sarman Singh, New Delhi (IN); Ramu Sivakumar, New Delhi (IN)

(73) Assignees: All India Institute of Medical Sciences, Division of Clinicial Microbiology, New Delhi (IN); Department of Biotechnology, Department of Govt of India, New Delhi (IN)

( * ) Notice: Subject to any disclaimer, the term of this patent is extended or adjusted under 35 U.S.C. 154(b) by 690 days.

(21) Appl. No.: 10/584,451

(22) PCT Filed: Dec. 26, 2003

(86) PCT No.: PCT/IN03/00400

§ 371 (c)(1),
(2), (4) Date: Jan. 23, 2007

(87) PCT Pub. No.: WO2005/063803

PCT Pub. Date: Jul. 14, 2005

(65) Prior Publication Data

US 2008/0031878 A1 Feb. 7, 2008

(51) Int. Cl.
*A61K 39/00* (2006.01)

(52) U.S. Cl. .................. 424/191.1; 435/7.1; 435/7.2; 435/7.22; 435/7.9; 435/7.92; 424/185.1; 424/269.1; 530/350

(58) Field of Classification Search .................. None
See application file for complete search history.

(56) References Cited

U.S. PATENT DOCUMENTS 5,834,592 A 11/1998 Reed et al.

2003/0162182 A1 8/2003 Salotra et al.

OTHER PUBLICATIONS

Kumar et al., Clinical and Diagnostic Laboratory Immunology, vol. 8, No. 6, pp. 1220-1224 (Nov. 2001).
Singh et al., J. Parasitol, vol. 81, No. 6, pp. 1000-1003 (1995).
Braz et al., Am J. Trop. Med. Hyg., vol. 67, No. 4, pp. 344-348 (2002).
Singh et al., Clinical and Diagnostic Laboratory Immunology, vol. 9, No. 3, pp. 568-572 (May 2002).
Badaro et al., The Journal of Infectious Diseases, vol. 173, pp. 758-761 (1996).
Qu et al., Transactions of the Royal Society of Tropical Medicine and Hygiene, vol. 88, No. 5, pp. 1-4 (1994).
Burns et al., Proc. Natl. Acad. Sci. USA, vol. 90, pp. 775-779 (Jan. 1993).

*Primary Examiner*—Jennifer E Graser
(74) *Attorney, Agent, or Firm*—Birch, Stewart, Kolasch & Birch, LLP

(57) ABSTRACT

The present invention provides compounds and methods for the detection of anti-leishmanial antibodies in individuals suspected of infection with the protozoan parasite of the genus *Leishmania*, where the infectious agent is an Indian strain and similar or closely related to Indian *Leishmania* strains. The compounds provided include polypeptides as shown in SEQ ID NO: 5 or SEQ ID NO: 6 which are useful for the detection of anti-leishmanial antibodies in individuals where the immune responses are elicited against *Leishmania* species of Indian strains and similar or closely related to Indian *Leishmania* strains, the compounds are also useful as a vaccine and therapeutic agent to prevent and treat leishmaniasis. The present invention further provides a diagnostic kit consisting of antibody raised against polypeptides as shown in SEQ ID NO: 5 or SEQ ID NO: 6 for detecting leishmanial antigens.

23 Claims, 11 Drawing Sheets

Figure 3A

Figure 1:
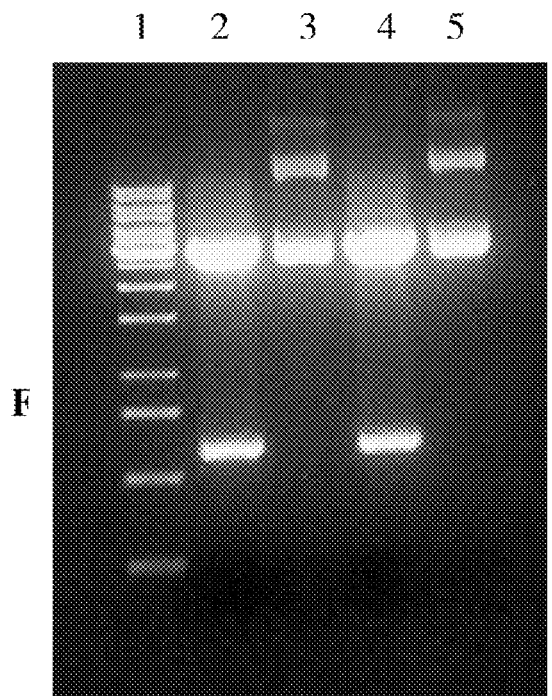

```
SEQ ID NO: 5   EGRAAELARKLEATASAKNLVEQDXXXXXXXXXXXXXXIAEVRAAELAGVLEATAAAKTAV 99
               E RAAELA +LEATA AK+  EQD              +E RAAELA  LEATAAAK +
SEQ ID NO: 12  EERAAELASQLEATAAAKSSAEQDRENTRATLEQQLRESEARAAELASQLEATAAAKMSA 771

SEQ ID NO: 5   EQERERTRAALXXXXXXXXXXXXXXXXXXXXXXXXXKTSVEQXXXXXXXXXXXXXXXXXXX 159
               EQ+RE TRA L                         K S EQ
SEQ ID NO: 12  EQDRENTRATLEQQLRDSEERAAELASQLESTTAAKMSAEQDRESTRATLEQQLRDSEER 831

SEQ ID NO: 5   XXXXXXXXKSTAAVKSAMEQDRENTRAT 187
                       +ST A K + EQDRE+TRAT
SEQ ID NO: 12  AAELASQLESTTAAKMSAEQDRESTRAT 859
```

Figure 3B

```
SEQ ID NO: 5   EQEREKTRTALE-------GRAAELARKLEATASAKNLVEQDXXXXXXXXXXXXXXIAEVR 81
               EQ+RE TR  LE       RAAELA +LEATA+AK    EQD              -E R
SEQ ID NO: 12  EQDRENTRATLEQQLRESEARAAELASQLEATAAAKMSAEQDRENTRATLEQQLRDSEER 792

SEQ ID NO: 5   AAELAGVLEATAAAKTAVEQERERTRAALXXXXXXXXXXXXXXXXXXXXXXXXXXXKTSVEQX 141
               AAELA  LE+T AAK + EQ+RE TRA L                            K S EQ
SEQ ID NO: 12  AAELASQLESTTAAKMSAEQDRESTRATLEQQLRDSEERAAELASQLESTTAAKMSAEQD 852

SEQ ID NO: 5   XXXXXXXXXXXXXXXXXXXXXXXXXXKSTAAVKSAMEQDRENTRAT 187
                                         +ST A K + EQDRE+TRAT
SEQ ID NO: 12  RESTRATLEQQLRESEERAAELASQLESTTAAKMSAEQDRESTRAT 898
```

Figure 3C

```
SEQ ID NO: 5   EQEREKTRTALEG-------RAAELARKLEATASAKNLVEQDXXXXXXXXXXXXXIAEVR  81
               EQ+RE TR  LE        RAAELA +LE+T +AK   EQD             +E R
SEQ ID NO: 12  EQDRENTRATLEQQLRDSEERAAELASQLESTTAAKMSAEQDRESTRATLEQQLRDSEER  831

SEQ ID NO: 5   AAELAGVLEATAAAKTAVEQERERTRAALXXXXXXXXXXXXXXXXXXXXXXXXXKTSVEQX  141
               AAELA   LE+T AAK +  EQ+RE TRA L                          K S EQ
SEQ ID NO: 12  AAELASQLESTTAAKMSAEQDRESTRATLEQQLRESEERAAELASQLESTTAAKMSAEQD  891

SEQ ID NO: 5   XXXXXXXXXXXXXXXXXXXXXXXXXXXKSTAAVKSAMEQDRENTRA  186
                                          ++TAA KS+ EQDRENTRA
SEQ ID NO: 12  RESTRATLEQQLRDSEERAAELASQLEATAAAKSSAEQDRENTRA   936
```

Figure 3D

```
SEQ ID NO: 5   EGRAAELARKLEATASAKNLVEQDXXXXXXXXXXXXXIAEVRAAELAGVLEATAAAKTAV  99
               E RAAELA +LEATA+AK+   EQD             +E RAAELA   LEATAAAK +
SEQ ID NO: 13  EERAAELASQLEATAAAKSSAEQDRENTRATLEQQLRESEARAAELASQLEATAAAKMSA  771

SEQ ID NO: 5   EQERERTRAALXXXXXXXXXXXXXXXXXXXXXXXXXXXXXXKTSVEQXXXXXXXXXXXXXXXXXXX  159
               EQ+RE TRA L                             K S EQ
SEQ ID NO: 13  EQDRENTRATLEQQLRDSEERAAELASQLESTTAAKMSAEQDRESTRATLEQQLRDSEER  831

SEQ ID NO: 5   XXXXXXXXKSTAAVKSAMEQDRENTRAT  187
                       +ST A K + EQDRE+TRAT
SEQ ID NO: 13  AAELASQLESTTAAKMSAEQDRESTRAT  859
```

Figure 3E

```
SEQ ID NO: 5   EQEREKTRTALE-------GRAAELARKLEATASAKNLVEQDXXXXXXXXXXXXXXIAEVR  81
               EQ+RE TR  LE       RAAELA +LEATA+AK   EQD              +E R
SEQ ID NO: 13  EQDRENTRATLEQQLRESEARAAELASQLEATAAAKMSAEQDRENTRATLEQQLRDSEER 792

SEQ ID NO: 5   AAELAGVLEATAAAKTAVEQERERTRAALXXXXXXXXXXXXXXXXXXXXXXXXXXKTSVEQX 141
               AAELA  LE+T AAK + EQ+RE TRA L                            K S EQ
SEQ ID NO: 13  AAELASQLESTTAAKMSAEQDRESTRATLEQQLRDSEERAAELASQLESTTAAKMSAEQD  852

SEQ ID NO: 5   XXXXXXXXXXXXXXXXXXXXXXXXXXXKSTAAVKSAMEQDRENTRAT 187
                                          +ST A K + EQDRE+TRAT
SEQ ID NO: 13  RESTRATLEQQLRESEERAAELASQLESTTAAKMSAEQDRESTRAT  898
```

Figure 3F

```
SEQ ID NO: 5   EQEREKTRTALEG-------RAAELARKLEATASAKNLVEQDXXXXXXXXXXXXXXIAEVR  81
               EQ+RE TR  LE        RAAELA +LE+T +AK   EQD              +E R
SEQ ID NO: 13  EQDRENTRATLEQQLRDSEERAAELASQLESTTAAKMSAEQDRESTRATLEQQLRDSEER 831

SEQ ID NO: 5   AAELAGVLEATAAAKTAVEQERERTRAALXXXXXXXXXXXXXXXXXXXXXXXXXXKTSVEQX 141
               AAELA  LE+T AAK + EQ+RE TRA L                            K S EQ
SEQ ID NO: 13  AAELASQLESTTAAKMSAEQDRESTRATLEQQLRESEERAAELASQLESTTAAKMSAEQD  891

SEQ ID NO: 5   XXXXXXXXXXXXXXXXXXXXXXXXXXXKSTAAVKSAMEQDRENTRA 186
                                          ++TAA KS+ EQDRENTRA
SEQ ID NO: 13  RESTRATLEQQLRDSEERAAELASQLEATAAAKSSAEQDRENTRA  936
```

Figure 4

```
SEQ ID NO: 14  121  GAGCAGCAGCTTCGCGAATCCGAGGCGCGCGCTGCGGAGCTGGCGAGCCAGCTGGAGGCC  180
SEQ ID NO:  4    1  ------------------------------------------------------------    1
SEQ ID NO: 15    1  GAGCAGCAGCTTCGTGAATCCGAGGCGCGCGCTGCGGAGCTGAAAGCCGAGCTGGAGGCC   60

SEQ ID NO: 14  181  ACTGCTGCTGCGAAGATGTCAGCGGAGCAGGACCGCGAGAACACGAGGGCCACGCTAGAG  240
SEQ ID NO:  4    1  ---------------------------------------------------------GAG    3
SEQ ID NO: 15   61  ACTGCTGCTGCGAAGACGTCGGTGGAGCAGGAGCGTGAGAAGAC-------------GAG  107

SEQ ID NO: 14  241  CAGCAGCTTCGTGACTCCGAGGAGCGCGCTGCGGAGCTGGCGAGCCAGCTGGAGTCCACT  300
SEQ ID NO:  4   64  CAGCAGCTTCGTGACTCCGAGGAGCGCGCTGCGGAGCTGATGCGGAAGTTAGAGGCGACT   63
SEQ ID NO: 15  108  GA-CGGCTCTG-------GAGGGGCGCGCTGCGGAGCTGGCTCGCAAACTGGAGGCGACT  159

SEQ ID NO: 14  301  ACTGCTGCGAAGATGTCAGCGGAGCAGGACCGCGAGAGCACGAGGGCCACGCTAGAGCAG  360
SEQ ID NO:  4   64  GCTGCTGCGAAGTCGTCGGCGGAGCAGGACCGCGAGAACACGAGGGCCACGTTGGAGCAG  123
SEQ ID NO: 15  160  GCTTCTGCGAAGAATTTGGTAGAGCAGGACCGCGAGAGGACGAGGGCCACCTTGGAGGAA  219

SEQ ID NO: 14  361  CAGCTTCGTGACTCCGAGGAGCGCGCTGCGGAGCTGGCGAGCCAGCTGGAGTCCACTACT  420
SEQ ID NO:  4  124  CAGCTTCGCGAATCCGAGGAGCACGCTGCGGAGCTGAAGGCCCAGCTGGAGTCCACTGCT  183
SEQ ID NO: 15  220  CGACTTCGTATTGCTGAGGTGCGCGCTGCGGAGCTGGCAGGAGTGCTGGAGGCCACTGCT  279

SEQ ID NO: 14  421  GCTGCGAAGATGTCAGCGGAGCAGGACCGCGAGAGCACGAGGGCCACGCTAGAGCAGCAG  480
SEQ ID NO:  4  184  GCTGCGAAGACGTCGGCGGAGCAGGACCGCGAGAACACGAGGGCCGCGTTGGAGCAGCGG  243
SEQ ID NO: 15  280  GCTGCGAAGACGGCGGTGGAGCAGGAGCGTGAGAGGACGAGGGCCGCCTTGGAGCAGCAG  339

SEQ ID NO: 14  481  CTTCGCGAATCCGAGGAGCGCGCTGCGGAGCTGGCGAGCCAGCTGGAGTCCACTACTGCT  540
SEQ ID NO:  4  244  CTTCGCGAATCCGAGGAGCGCGCTGCGGAGCTGGCGAGCCAGCTGGAGGCCACTGCTGCT  303
SEQ ID NO: 15  340  CTCCGCGAATCCGAGGCGCGCGCTGCGGAGCTGGCTGCGCAGCTGGAAGCCGCTGCTGCG  399

SEQ ID NO: 14  541  GCGAAGATGTCAGCGGAGCAGGACCGCGAGAGCACGAGGGCCACGCTAGAGCAGCAGCTT  600
SEQ ID NO:  4  304  GCGAAGTCGTCGGCGGAGCAGGACCGCGAGAACACGAGGGCCACGCTAGAGCAGCAGCTT  363
SEQ ID NO: 15  400  GCGAAGACGTCGGTGGAGCAGGAGCGTGAGAACACGAGGGCCACCTTGGAGGAGCGGTTG  459

SEQ ID NO: 14  601  CGTGACTCCGAGGAGCGCGCTGCGGAGCTGGCGAGCCAGCTGGAGGCCACTGCTGCTGCG  660
SEQ ID NO:  4  364  CGCGAATCCGAGGCGCGCGCTGCGGAGCTGGCGAGTCAGCTGGAGTCCACTGCTGCTGCG  423
SEQ ID NO: 15  460  CGGCTCGCTGAGGTCCGCGCTGCGGAGCTGGCAGCGCGGCTAAAGAGCACTGCTGCTGTT  519

SEQ ID NO: 14  661  AAGTCGTCGGCGGAGCAGGACCGCGAGAACACGAGGGCCGCGTTGGAGCAGCAGCTTCGT  720
SEQ ID NO:  4  424  AAGTCGTCGGCGGAGCAGGACCGCGAGAACACGAGGGCCACG------------------  465
SEQ ID NO: 15  520  AAGTCCGCGATGGAGCAGGACCGCGAGAACACGAGGGCCACG------------------  561
```

Figure 5

```
SEQ ID NO: 16    1  LEQQLRESEERAAELASQLEATAAAKSSAEQDRENTRATLEQQLRESEARAAELASQLEA  60
SEQ ID NO:  6    1  -EQQLRESEERAAELMRKLEATAAAKSSAEQDRENTRATLEQQLRESEEHAAELKAQLES  59
SEQ ID NO:  5    1  -EQQLRESEARAAELKAELEATAAAKTSVEQDREKTRTALEG-------RAAELARKLEA  52

SEQ ID NO: 16   61  TAAAKMSAEQDRENTRATLEQQLRDSEERAAELASQLESTTAAKMSAEQDRESTRATLEQ 120
SEQ ID NO:  6   60  TAAAKTSAEQDRENTRAALEQRLRESEERAAELASQLESTAAAKSSAEQDRENTRATLEQ 119
SEQ ID NO:  5   53  TASAKNLVEQDRERTRATLEERLRIAEVRAAELAGVLEATAAAKTAVEQRERTRAALEQ 112

SEQ ID NO: 16  121  QLRSSEERAAELASQLESTTAAKMSAEQDRESTRATLEQQLRESEERAAELASQLESTTA 180
SEQ ID NO:  6  120  QLRESEARAAELASQLESTAAAKSSAEQDRENTRAT------------------------ 155
SEQ ID NO:  5  113  QLRESEARAAELAQLEAAAAKTSVEQRENTRATLEERLRLAEVRAAELAARLKSTAA 172

SEQ ID NO: 16  181  AKMSAEQDRESTRATLEQQLRDSEERAAELASQLEATAAAKSSAEQDRENTRAALEQQLR 240
SEQ ID NO:  6  155  ------------------------------------------------------------ 155
SEQ ID NO:  5  173  VKSAMEQDRENTRAT--------------------------------------------- 187
```

Figure 6

```
SEQ ID NO: 16    1  LEQQLRESEERAAELASQLEATAAAKSSAEQDRENTRATLEQQLRESEARAAELASQLEA  60
SEQ ID NO:  5    1  ---------------------------------------EQQLRESEARAAELKAELEA  20

SEQ ID NO: 16   61  TAAAKMSAEQDRENTRATLEQQLRDSEERAAELASQLESTTAKMSAEQDRESTRATLEQ 120
SEQ ID NO:  5   21  TAAAKTSVEQDREKTRTALEG-------RAAELARKLEATASAKNLVEQDRERTRATLE  73

SEQ ID NO: 16  121  QLRDSEERAAELASQLESTTAAKMSAEQDRESTRATLEQQLRESEERAAELASQLESTTA 180
SEQ ID NO:  5   74  RLRIAEVRAAELAGVLEATAAAKTAVEQRERTRAALEQQLRESEARAAELAAQLEAAAA 133

SEQ ID NO: 16  181  AKMSAEQDRESTRATLEQQLRDSEERAAELASQLEATAAAKSSAEQDRENTRAALEQQLR 240
SEQ ID NO:  5  134  AKTSVEQRENTRATLEERLRLAEVRAAELAARLKSTAAVKSAMEQDRENTRAT------ 187
```

Figure 7

```
SEQ ID NO: 6   1  EQQLRDSEERAAELMRKLEATAAAKSSAEQ------------------------------  30
SEQ ID NO: 5   1  EQQLRDSEARAAELKAELEATAAAKTSVEQEREKTRTALEGRAAELARKLEATASAKNLV  60

SEQ ID NO: 6  30  --DRENTRATLEQLRESEEHAAELKAQLESTAAAKTSAEQRENTRAALEQRLRESEER    88
SEQ ID NO: 5  61  EQDRERTRATLEERLRIAEVRAAELAGVLESTAAAKTSVEQRERTRAALEQCLRESEAR  120

SEQ ID NO: 6  89  AAELAQLEATAAAKSSAEQDRENTRATLEQLRESEARAAELAQLESTAAAKSSAEQD   148
SEQ ID NO: 5 121  AAELAAQLEAAAAKTSVEQRENTRATLEERLREVRAAELARLKSTAAVKSAMEQD    180

SEQ ID NO: 6 149  RENTRAT 155
SEQ ID NO: 5 181  RENTRAT 187
```

Figure 8

Figure 9

Figure 10
a)
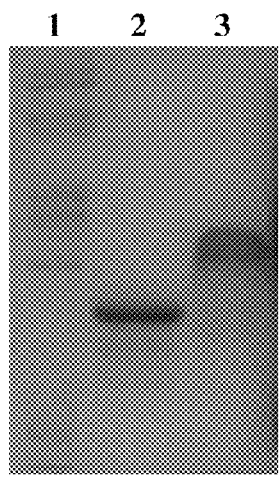
b)
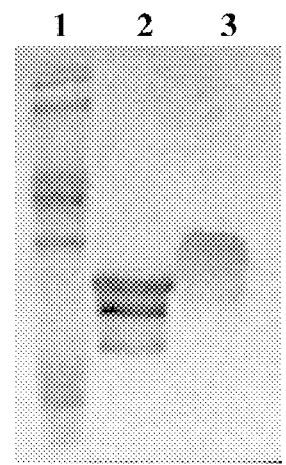
Figure 11
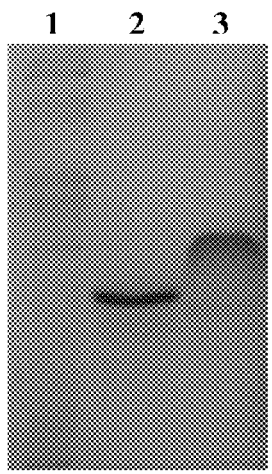
b)
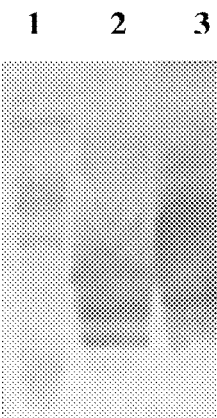

Figure 12
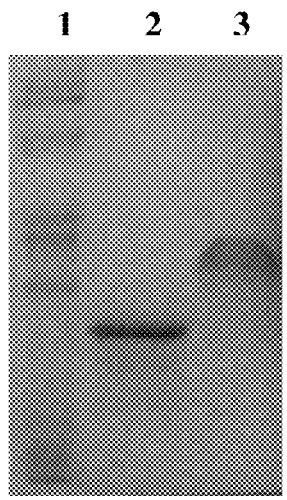
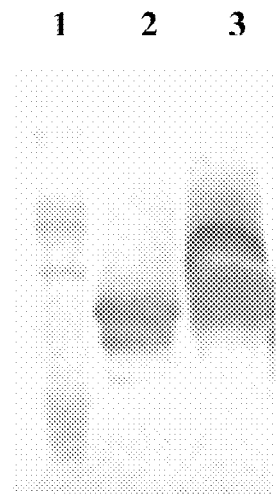
b)
Figure 13
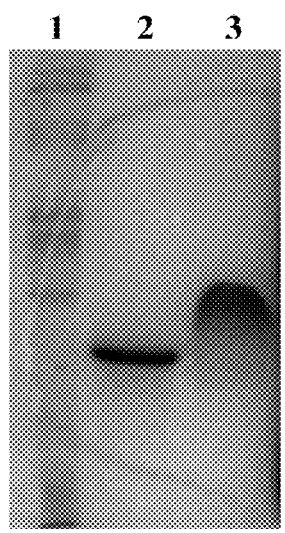
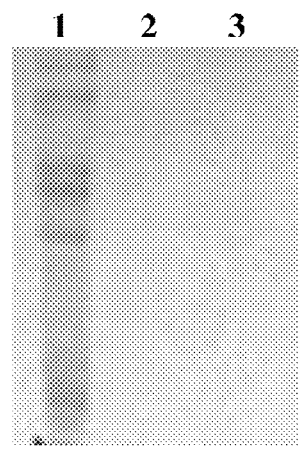
b)

SEQUENCE LISTING

<160> NUMBER OF SEQ ID NOS: 16

<210> SEQ ID NO 1
<211> LENGTH: 3016
<212> TYPE: DNA
<213> ORGANISM: Leishmania donovani

<400> SEQUENCE: 1

-continued

```
cggcgcgtcg gtgtctttga ttccactgat caccgcctcg ccatatgctc atcgtggtcc    60
aacgcgaccc ccctccccca aaggcaagcg agacgtatcg accatgccgt ctgcccgcat   120
ctgtgcttaa caagcgagcc aggtgtccct tccgcagctc cgaatctttc gcgtggcgcc   180
acacactgta tgagcgtcac taccccttgta tacctcagac cacttcccgc cgcccctcta   240
cccttctaca cgcctacaca cacatatgta tacatgaaca tctctcagca cacaacgcac   300
acatactgtg accggtatta ctgcaccaac gtctacctct tccacgatgc acccttctac   360
tgtgcggcgt gaggcggagc gggtgaaggt gtcggtgcgc gtgcgccccc tcaacgaccg   420
tgaaaacaat actgccgaag gggcgaaagt caccgtcgcg gcgaaacagg cggcggccgt   480
ggtaaccgtc aagttcatgg gaggcaccag caacagctgc cccgccgagt cggggggctgc   540 gaggcgggta acgcaggact ccagttcga ccacgtgttc tggtctctgg agacgccgga   600
cgcgtgtggc gcgacccctg cgacgcaggc agacgtgttc cggacgatcg ggtacccgct   660
ggtgcagcac gcgttcgacg ggttcaactc gtgcctgttt gcgtacgggc agacggggag   720
cgggaagacg tacacgatga tgggtgcgga cgtgagcgcg cttagcggtg agggcagcgg   780
cgtgacgccg cggatctgcc tggagatctt tgcgcggaag gcgagcgtgg aggcacaggg   840
gcactcgcgg tggattgtgg agcccgggta cgtggaggtg tacaacgagc gcgtgtcgga   900
cctgcttggg aagcggaaga agggcgcgaa gggcggcatc gaggaggtgt acgtggacgt   960
gcgcgagcac ccgagccgcg gcgtgttcct ggaggggcag cggctggtgg aggttgggag  1020
cctggacgat gttgtgcggc tgatcgaggc cggcaacagc gtgcggcaca cggcctcgac  1080
gaagatgaac gaccggagca gccgtagcca cgcgatcatc atgctgctgc tgcgcgagga  1140
gcggacgatg acgacgaagg gcggagagac gatccgtact gccggcaaga gcagccgcat  1200
gaaccttgtg gaccttgcgg ggtctgagcg cgtggcgcag tcgcaggtgg agggacagca  1260
gttcaaggag gcgacgcaca tcaacctgtc gctgacgacg ctcgggcgtg tgatcgacgt  1320
gctcgcggac atggcaacga agggcgcgaa acacagtac agcgttccgc cgttccgcga  1380
ctcgaagctg acgttcatcc tgaaggactc gcttggcggg aactcgaaga cgttcatggt  1440
tgcgactgtg agcccgagcg cgctgaacta cgaggagacg ctgagcacgc tgcggtacgc  1500
gtcgcgcgcg cgcgacattg tgaacgttgc gcaggtgaac gaggaccgc gcgcgcgtcg  1560 gatccgcgag ctggaggagc agatggagga catgcggcag gcgatggctg cggtgacccc  1620
cgcgtacgtg tctgagctga agaagaagct tgcgctgctg gagtcggagg cgcagaagtg  1680
tgcggcggac ctgcaggcgc tagagcggga gcgggagcac aaccaggtgc aggagcggct  1740
gctgcgcgcc acggaggcgg agaagagcga gctggagtcg cgtgcggctg cgctgcagga  1800
ggagatgacc gcgacgcgac agcaggcaga caagatgcag gcgctaaacc ttcggctgaa  1860
ggaagagcag gcgcgcaagg agcgagagct actgaaagag atggcgaaga aggacgccgc  1920
gctctcgaag gttcggcggc gcaaggatgc cgagatcgca agcgagcgcg agaagttgga  1980
gtcgaccgtg gcgcagcttg agcgtgaaca gcgcgagcgc gaggtcgctc tggacgcatt  2040
gcagacgcac cagagaaagc tgcaggaagc gctcgagagc tctgagcgga cagccgcgga  2100
aagggaccag cttctgcagc agcttacaga gcttcagtct gagcgtgcgc agctatcaca  2160
ggttgtcagc gaccgcgagc ggctgacccg cgacttgcag cgtattcagt ccgagtacgg  2220
ggaaacggag ctcgcgcgag acgcggcgct gtgcgccgca caggagatgg aggcgcgcta  2280
tcacgctgct gtgtttcacc tgcaaacgct cctggagctc gcaaccgagt gggaggatgc  2340
```

-continued

| | |
|---|---|
| gctccgcgag cgtgcgcttg cagagcgtga cgaagccgct gcagctgaac ttgatgccgc | 2400 |
| agcttctact tctgaaaacg cacgggaaag cacttccaag ctgctaacca gcgttgagca | 2460 |
| gcagcttcgt gaatccgagg cgcgcgctgc ggagctgaaa gccgagctgg aggccactgc | 2520 |
| tgctgcgaag acgtcggtgg agcaggagcg tgagaagacg aggacggctc tggaggggcg | 2580 |
| cgctgcggag ctggctcgca aactggaggc gactgcttct gcgaagaatt tggtagagca | 2640 |
| ggaccgcgag aggacgaggg ccaccttgga ggaacgactt cgtattgctg aggtgcgcgc | 2700 |
| tgcggagctg gcaggagtgc tggaggccac tgctgctgcg aagacggcgg tggagcagga | 2760 |
| gcgtgagagg acgagggccg ccttggagca gcagctccgc gaatccgagg cgcgcgctgc | 2820 |
| ggagctggct gcgcagctgg aagccgctgc tgcggcgaag acgtcggtgg agcaggagcg | 2880 |
| tgagaacacg agggccacct tggaggagcg gttgcggctc gctgaggtcc gcgctgcgga | 2940 |
| gctggcagcg cggctaaaga gcactgctgc tgttaagtcc gcgatggagc aggaccgcga | 3000 |
| gaacacgagg gccacg | 3016 |

<210> SEQ ID NO 2
<211> LENGTH: 2937
<212> TYPE: DNA
<213> ORGANISM: Leishmania donovani

<400> SEQUENCE: 2

| | |
|---|---|
| cggcgcgtcg gtgtctttga ttgcacagct caccgcctcg ccatattttc gtcgtggcca | 60 |
| cgcgaccccc cgaccttccc ctcctccgcc cccaaagaca agccagacat accgaccatg | 120 |
| ccgtctgccc gcgtctctgc ttaccaagcg cgccacgcac cccttcctcg gccctgaatc | 180 |
| tttcgcgcgg cgccatacat tgcatgcacg tcactacgcc tgtacacctt acacctcctc | 240 |
| ttgcccaccc ctttcccctt ctacacgcct aactacacac acacacatat atatatataa | 300 |
| agcgctcaac gcacacatac tgtggccagt attactgcac caacgtctgc ctcttccagg | 360 |
| atgcacccct ccactgtgcg gcgtgaggcg agcgggtga aggtgtcggt gcgcgtgcgc | 420 |
| cccctaaacg aacgtgaaaa caatgccccg gaagggacga aagtgaccgt tgcggcgaaa | 480 |
| caggcggccg ccgtggtgac ggtcaaggtc ctgggaggca gcaacaacag cggcgccgcc | 540 |
| gagtcgatgg ggactgcaag gcgggtagcg caggactttc agttcgacca cgtgttctgg | 600 |
| tctgtggaga cgccggacgc gtgcggcgcg acccccgcga cgcaggcaga cgtgttccgg | 660 |
| acgatcgggt acccgctggt gcagcacgcg ttcgacgggt tcaactcgtg cttgtttgcg | 720 |
| tacgggcaga cagggagcgg gaagatgtac acgatgatgg gcgcggacgt gagcgcgctt | 780 |
| agtggtgagg gcaacggcgt gacgccgcgg atctgcctgg agatctttgc gcggaaggcg | 840 |
| agcgtggagg cgcaggggca ctcgcggtgg atcgtggagc tggggtacgt ggaggtgtac | 900 |
| aacgagcgcg tgtcggacct gcttgggaag cggaagaagg gtgtgaaggg cggcggcgag | 960 |
| gaggtgtacg tggacgtgcg cgagcacccg agccgcggcg tgttcctgga ggggcagcgg | 1020 |
| ctggtggagg ttgggagcct ggacgatgtt gtgcggctga tcgagatcgg caacggcgtg | 1080 |
| cggcacaccg cttcaacgaa gatgaacgac cggagcagcc ggagccacgc gatcatcatg | 1140 |
| ctgctgctgc gcgaggagcg gacgatgacg acgaagagcg gggagacgat ccgtactgcc | 1200 |
| ggcaagagca gccgcatgaa ccttgtggac cttgcgggt ctaagcgcgt ggcgcagtcg | 1260 |
| caggtggagg ggcagcagtt caaggaggcg acgcacatca acctgtcgct gacgacgctc | 1320 |
| gggcgcgtga tcgacgtgct cgcggacatg gcgacgaagg gtgcgaaggc gcagtacagc | 1380 |
| gttgcgccgt tccgcgactc gaagctgacg ttcatcctga aggactcgct tggcgggaac | 1440 |

```
tcgaagacgt tcatgatcgc gactgtgagc ccgagcgcgc tgaactacga ggagacgctg    1500
agcacgctgc ggtacgcgtc gcgcgcgcgc gacattgtga atgttgcgca ggtgaacgag    1560
gacccgcgcg cacggcggat ccgcgagctg gaggagcaga tggaggacat gcggcaggcg    1620
atggctggcg gcgaccccgc gtacgtgtcg gagctgaaga agaagcttgc gctgctggag    1680
tcggaggcgc agaagcgtgc ggcggacctg caggcgctgg agggagcg ggagcacaac    1740 caggtgcagg agcggctgct gcgcgcgacg gaggcggaga gagcgagct ggagtcgcgt    1800 gcggctgcgc tgcaggagga gatgaccgcg actcgacggc aggcggacaa gatgcaggcg    1860
ctgaacctgc ggctgaagga gagcaggcg cgcaaggagc gcgagctgct gaaagagatg    1920
gcgaagaagg acgccgcgct ctcgaaggtt cggcaacgca aagacgccga gatagcaagc    1980
gagcgcgaga agctggagtc gaccgtggcg cagctggagc gtgagcagcg cgagcgcgag    2040
gtggctctgg acgcattgca gacgcaccag agaaagctgc aggaagcgct cgagagctct    2100
gagcggacag ccgcggaaag ggaccagctg ctgcagcagc taacagagct tcagtctgag    2160
cgtacgcagc tatcacaggt tgtgaccgac cgcgagcggc ttacacgcga cttgcagcgt    2220
attcagtacg agtacgggga aaccgagctc gcgcgagacg tggcgctgtg cgccgcgcag    2280
gagatggagg cgcgctacca cgctgctgtg tttcacctgc aaacgctcct ggagctcgca    2340
accgagtggg aggacgcact ccgcgagcgt gcgcttgcag agcgtgacga agccgctgca    2400
gccgaacttg atgccgcagc ctctacttcc caaaacgcac gtgaaagcgc ctgcgagcgg    2460
ctaaccagcc ttgagcagca gcttcgtgac tccgaggagc gcgctgcgga gctgatgcgg    2520
aagttagagg cgactgctgc tgcgaagtcg tcggcggagc aggaccgcga gaacacgagg    2580
gccacgttgg agcagcagct tcgcgaatcc gaggagcacg ctgcggagct gaaggcccag    2640
ctggagtcca ctgctgctgc gaagacgtcg gcggagcagg accgcgagaa cacgagggcc    2700
gcgttggagc agcggcttcg cgaatccgag gagcgcgctg cggagctggc gagccagctg    2760
gaggccactg ctgctgcgaa gtcgtcggcg gagcaggacc gcgagaacac gagggccacg    2820
ctagagcagc agcttcgcga atccgaggcg cgcgctgcgg agctggcgag tcagctggag    2880
tccactgctg ctgcgaagtc gtcggcggag caggaccgcg agaacacgag ggccacg      2937
```

<210> SEQ ID NO 3
<211> LENGTH: 563
<212> TYPE: DNA
<213> ORGANISM: Leishmania donovani

<400> SEQUENCE: 3

```
tcgtggccct cgtgttctcg cggtcctgct ccatcgcgga cttaacagca gcagtgctct     60
ttagccgcgc tgccagctcc gcagcgcgga cctcagcgag ccgcaaccgc tcctccaagg    120
tggccctcgt gttctcacgc tcctgctcca ccgacgtctt cgccgcagca gcggcttcca    180
gctgcgcagc cagctccgca gcgcgcgcct cggattcgcg gagctgctgc tccaaggcgg    240
ccctcgtcct ctcacgctcc tgctccaccg ccgtcttcgc agcagcagtg gcctccagca    300
ctcctgccag ctccgcagcg cgcacctcag caatacgaag tcgttcctcc aaggtggccc    360
tcgtcctctc gcggtcctgc tctaccaaat tcttcgcaga agcagtcgcc tccagtttgc    420
gagccagctc cgcagcgcgc ccctccagag ccgtcctcgt cttctcacgc tcctgctcca    480
ccgacgtctt cgcagcagca gtggcctcca gctcggcttt cagctccgca gcgcgcgtct    540
cggagtcacg aagctgctgc tca                                            563
```

<210> SEQ ID NO 4
<211> LENGTH: 466
<212> TYPE: DNA
<213> ORGANISM: Leishmania donovani

<400> SEQUENCE: 4

```
gagcagcagc ttcgtgactc cgaggagcgc gctgcggagc tgatgcggaa gttagaggcg      60
actgctgctg cgaagtcgtc ggcggagcag gaccgcgaga cacgagggc cacgttggag      120
cagcagcttc gcgaatccga ggagcacgct gcggagctga aggcccagct ggagtccact      180
gctgctgcga agacgtcggc ggagcaggac cgcgagaaca cgagggccgc gttggagcag      240
cggcttcgcg aatccgagga gcgcgctgcg gagctggcga ccagctggag ggccactgct      300
gctgcgaagt cgtcggcgga gcaggaccgc gagaacacga gggccacgct agagcagcag      360
cttcgcgaat ccgaggcgcg cgctgcggag ctggcgagtc agctggagtc cactgctgct      420
gcgaagtcgt cggcggagca ggaccgcgag aacacgaggg ccacga                   466
```

<210> SEQ ID NO 5
<211> LENGTH: 187
<212> TYPE: PRT
<213> ORGANISM: Leishmania donovani

<400> SEQUENCE: 5

```
Glu Gln Gln Leu Arg Glu Ser Glu Ala Arg Ala Ala Glu Leu Lys Ala
1               5                   10                  15

Glu Leu Glu Ala Thr Ala Ala Lys Thr Ser Val Glu Gln Glu Arg
            20                  25                  30

Glu Lys Thr Arg Thr Ala Leu Glu Gly Arg Ala Ala Glu Leu Ala Arg
        35                  40                  45

Lys Leu Glu Ala Thr Ala Ser Ala Lys Asn Leu Val Glu Gln Asp Arg
    50                  55                  60

Glu Arg Thr Arg Ala Thr Leu Glu Glu Arg Leu Arg Ile Ala Glu Val
65                  70                  75                  80

Arg Ala Ala Glu Leu Ala Gly Val Leu Glu Ala Thr Ala Ala Ala Lys
                85                  90                  95

Thr Ala Val Glu Gln Glu Arg Glu Arg Thr Arg Ala Ala Leu Glu Gln
            100                 105                 110

Gln Leu Arg Glu Ser Glu Ala Arg Ala Ala Glu Leu Ala Ala Gln Leu
        115                 120                 125

Glu Ala Ala Ala Ala Lys Thr Ser Val Gln Glu Arg Glu Asn
    130                 135                 140

Thr Arg Ala Thr Leu Glu Glu Arg Leu Arg Leu Ala Glu Val Arg Ala
145                 150                 155                 160

Ala Glu Leu Ala Ala Arg Leu Lys Ser Thr Ala Ala Val Lys Ser Ala
                165                 170                 175

Met Glu Gln Asp Arg Glu Asn Thr Arg Ala Thr
            180                 185
```

<210> SEQ ID NO 6
<211> LENGTH: 155
<212> TYPE: PRT
<213> ORGANISM: Leishmania donovani

<400> SEQUENCE: 6

```
Glu Gln Gln Leu Arg Asp Ser Glu Glu Arg Ala Ala Glu Leu Met Arg
1               5                   10                  15
```

-continued

| | | | | | | | | | | | |
|---|---|---|---|---|---|---|---|---|---|---|---|
|Lys|Leu|Glu|Ala|Thr|Ala|Ala|Lys|Ser|Ser|Ala|Glu|Gln|Asp|Arg|
| | |20| | | |25| | | |30| |

Glu Asn Thr Arg Ala Thr Leu Glu Gln Gln Leu Arg Glu Ser Glu Glu
       35              40             45

His Ala Ala Glu Leu Lys Ala Gln Leu Glu Ser Thr Ala Ala Ala Lys
 50                55                60

Thr Ser Ala Glu Gln Asp Arg Glu Asn Thr Arg Ala Ala Leu Glu Gln
65              70                75               80

Arg Leu Arg Glu Ser Glu Glu Arg Ala Ala Glu Leu Ala Ser Gln Leu
          85             90               95

Glu Ala Thr Ala Ala Lys Ser Ser Ala Glu Gln Asp Arg Glu Asn
        100            105           110

Thr Arg Ala Thr Leu Glu Gln Gln Leu Arg Glu Ser Glu Ala Arg Ala
        115            120           125

Ala Glu Leu Ala Ser Gln Leu Glu Ser Thr Ala Ala Ala Lys Ser Ser
        130            135           140

Ala Glu Gln Asp Arg Glu Asn Thr Arg Ala Thr
145              150              155

```
<210> SEQ ID NO 7
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 7
cggcgcgtcg gtgtctttga t                                            21

<210> SEQ ID NO 8
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 8
aggtccgccg cacgcttctg                                              20

<210> SEQ ID NO 9
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 9
gcgggaactc gaagacgttc at                                           22

<210> SEQ ID NO 10
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 10
gagcagcagc ttcgtgactc c                                            21

<210> SEQ ID NO 11
<211> LENGTH: 20
<212> TYPE: DNA
```

<213> ORGANISM: Artificial Sequence
<220> FEATURE:
<223> OTHER INFORMATION: Synthetic Sequence

<400> SEQUENCE: 11
cgtggccctc gtgttctcgc                                                          20

<210> SEQ ID NO 12
<211> LENGTH: 955
<212> TYPE: PRT
<213> ORGANISM: Unknown
<220> FEATURE:
<223> OTHER INFORMATION: Synthetic sequence from US patents 5411865 and
      5719263

<400> SEQUENCE: 12

Met His Pro Ser Thr Val Arg Arg Glu Ala Glu Arg Val Lys Val Ser
1               5                   10                  15

Val Arg Val Arg Pro Leu Asn Glu Arg Glu Asn Asn Ala Pro Glu Gly
            20                  25                  30

Thr Lys Val Thr Val Ala Ala Lys Gln Ala Ala Ala Val Val Thr Val
        35                  40                  45

Lys Val Leu Gly Gly Ser Asn Asn Ser Gly Ala Ala Glu Ser Met Gly
    50                  55                  60

Thr Ala Arg Arg Val Ala Gln Asp Phe Gln Phe Asp His Val Phe Trp
65                  70                  75                  80

Ser Val Glu Thr Pro Asp Ala Cys Gly Ala Thr Pro Ala Thr Gln Ala
                85                  90                  95

Asp Val Phe Arg Thr Ile Gly Tyr Pro Leu Val Gln His Ala Phe Asp
            100                 105                 110

Gly Phe Asn Ser Cys Leu Phe Ala Tyr Gly Gln Thr Gly Ser Gly Lys
        115                 120                 125

Thr Tyr Thr Met Met Gly Ala Asp Val Ser Ala Leu Ser Gly Glu Gly
    130                 135                 140

Asn Gly Val Thr Pro Arg Ile Cys Leu Glu Ile Phe Ala Arg Lys Ala
145                 150                 155                 160

Ser Val Glu Ala Gln Gly His Ser Arg Trp Ile Val Glu Leu Gly Tyr
                165                 170                 175

Val Glu Val Tyr Asn Glu Arg Val Ser Asp Leu Leu Gly Lys Arg Lys
            180                 185                 190

Lys Gly Val Lys Gly Gly Glu Val Tyr Val Asp Val Arg Glu
            195                 200                 205

His Pro Ser Arg Gly Val Phe Leu Glu Gly Gln Arg Leu Val Glu Val
            210                 215                 220

Gly Ser Leu Asp Asp Val Val Arg Leu Ile Glu Ile Gly Asn Gly Val
225                 230                 235                 240

Arg His Thr Ala Ser Thr Lys Met Asn Asp Arg Ser Ser Arg Ser His
                245                 250                 255

Ala Ile Ile Met Leu Leu Leu Arg Glu Glu Arg Thr Met Thr Thr Lys
            260                 265                 270

Ser Gly Glu Thr Ile Arg Thr Ala Gly Lys Ser Ser Arg Met Asn Leu
        275                 280                 285

Val Asp Leu Ala Gly Ser Glu Arg Val Ala Gln Ser Gln Val Glu Gly
    290                 295                 300

Gln Gln Phe Lys Glu Ala Thr His Ile Asn Leu Ser Leu Thr Thr Leu
305                 310                 315                 320

-continued

```
Gly Arg Val Ile Asp Val Leu Ala Asp Met Ala Thr Lys Gly Ala Lys
                325                 330                 335

Ala Gln Tyr Ser Val Ala Pro Phe Arg Asp Ser Lys Leu Thr Phe Ile
            340                 345                 350

Leu Lys Asp Ser Leu Gly Gly Asn Ser Lys Thr Phe Met Ile Ala Thr
        355                 360                 365

Val Ser Pro Ser Ala Leu Asn Tyr Glu Glu Thr Leu Ser Thr Leu Arg
    370                 375                 380

Tyr Ala Ser Arg Ala Arg Asp Ile Val Asn Val Ala Gln Val Asn Glu
385                 390                 395                 400

Asp Pro Arg Ala Arg Arg Ile Arg Glu Leu Glu Glu Gln Met Glu Asp
                405                 410                 415

Met Arg Gln Ala Met Ala Gly Gly Asp Pro Ala Tyr Val Ser Glu Leu
            420                 425                 430

Lys Lys Lys Leu Ala Leu Leu Glu Ser Glu Ala Gln Lys Arg Ala Ala
        435                 440                 445

Asp Leu Gln Ala Leu Glu Arg Glu Arg Glu His Asn Gln Val Gln Glu
    450                 455                 460

Arg Leu Leu Arg Ala Thr Glu Ala Glu Lys Ser Glu Leu Glu Ser Arg
465                 470                 475                 480

Ala Ala Ala Leu Gln Glu Glu Met Thr Ala Thr Arg Arg Gln Ala Asp
                485                 490                 495

Lys Met Gln Ala Leu Asn Leu Arg Leu Lys Glu Gln Ala Arg Lys
            500                 505                 510

Glu Arg Glu Leu Leu Lys Glu Met Ala Lys Asp Ala Ala Leu Ser
        515                 520                 525

Lys Val Arg Arg Arg Lys Asp Ala Glu Ile Ala Ser Glu Arg Glu Lys
    530                 535                 540

Leu Glu Ser Thr Val Ala Gln Leu Glu Arg Glu Gln Arg Glu Arg Glu
545                 550                 555                 560

Val Ala Leu Asp Ala Leu Gln Thr His Gln Arg Lys Leu Gln Glu Ala
                565                 570                 575

Leu Glu Ser Ser Glu Arg Thr Ala Ala Glu Arg Asp Gln Leu Leu Gln
            580                 585                 590

Gln Leu Thr Glu Leu Gln Ser Gly Arg Thr Gln Leu Ser Gln Val Val
        595                 600                 605

Thr Asp Arg Glu Arg Leu Thr Arg Asp Leu Gln Arg Ile Gln Tyr Glu
    610                 615                 620

Tyr Gly Glu Thr Glu Leu Ala Arg Asp Val Ala Leu Cys Ala Ala Gln
625                 630                 635                 640

Glu Met Glu Ala Arg Tyr His Ala Ala Val Phe His Leu Gln Thr Leu
                645                 650                 655

Leu Glu Leu Ala Thr Glu Trp Glu Asp Ala Leu Arg Glu Arg Ala Leu
            660                 665                 670

Ala Glu Arg Asp Glu Ala Ala Ala Glu Leu Asp Ala Ala Ala Ser
        675                 680                 685

Thr Ser Gln Asn Ala Arg Glu Ser Ala Cys Glu Arg Leu Thr Ser Leu
    690                 695                 700

Glu Gln Gln Leu Arg Glu Ser Glu Glu Arg Ala Ala Glu Leu Ala Ser
705                 710                 715                 720

Gln Leu Glu Ala Thr Ala Ala Lys Ser Ser Ala Glu Gln Asp Arg
                725                 730                 735

Glu Asn Thr Arg Ala Thr Leu Glu Gln Gln Leu Arg Glu Ser Glu Ala
```

-continued

```
                740                 745                 750
Arg Ala Ala Glu Leu Ala Ser Gln Leu Glu Ala Thr Ala Ala Lys
        755                 760                 765
Met Ser Ala Glu Gln Asp Arg Glu Asn Thr Arg Ala Thr Leu Glu Gln
    770                 775                 780
Gln Leu Arg Asp Ser Glu Arg Ala Ala Glu Leu Ala Ser Gln Leu
785                 790                 795                 800
Glu Ser Thr Thr Ala Ala Lys Met Ser Ala Glu Gln Asp Arg Glu Ser
            805                 810                 815
Thr Arg Ala Thr Leu Glu Gln Gln Leu Arg Asp Ser Glu Glu Arg Ala
                820                 825                 830
Ala Glu Leu Ala Ser Gln Leu Glu Ser Thr Thr Ala Ala Lys Met Ser
        835                 840                 845
Ala Glu Gln Asp Arg Glu Ser Thr Arg Ala Thr Leu Glu Gln Gln Leu
    850                 855                 860
Arg Glu Ser Glu Glu Arg Ala Ala Glu Leu Ala Ser Gln Leu Glu Ser
865                 870                 875                 880
Thr Thr Ala Ala Lys Met Ser Ala Glu Gln Asp Arg Glu Ser Thr Arg
            885                 890                 895
Ala Thr Leu Glu Gln Gln Leu Arg Asp Ser Glu Glu Arg Ala Ala Glu
                900                 905                 910
Leu Ala Ser Gln Leu Glu Ala Thr Ala Ala Lys Ser Ser Ala Glu
        915                 920                 925
Gln Asp Arg Glu Asn Thr Arg Ala Ala Leu Glu Gln Gln Leu Arg Asp
    930                 935                 940
Ser Glu Glu Arg Ala Ala Glu Leu Ala Ser Gln
945                 950                 955

<210> SEQ ID NO 13
<211> LENGTH: 955
<212> TYPE: PRT
<213> ORGANISM: Unknown
<220> FEATURE:
<223> OTHER INFORMATION: Synthetic sequence from US patent 5912166

<400> SEQUENCE: 13

Met His Pro Ser Thr Val Arg Arg Glu Ala Glu Arg Val Lys Val Ser
1               5                   10                  15
Val Arg Val Arg Pro Leu Asn Glu Arg Glu Asn Asn Ala Pro Glu Gly
            20                  25                  30
Thr Lys Val Thr Val Ala Ala Lys Gln Ala Ala Val Val Thr Val
        35                  40                  45
Lys Val Leu Gly Gly Ser Asn Asn Ser Gly Ala Ala Glu Ser Met Gly
    50                  55                  60
Thr Ala Arg Arg Val Ala Gln Asp Phe Gln Phe Asp His Val Phe Trp
65                  70                  75                  80
Ser Val Glu Thr Pro Asp Ala Cys Gly Ala Thr Pro Ala Thr Gln Ala
                85                  90                  95
Asp Val Phe Arg Thr Ile Gly Tyr Pro Leu Val Gln His Ala Phe Asp
            100                 105                 110
Gly Phe Asn Ser Cys Leu Phe Ala Tyr Gly Gln Thr Gly Ser Gly Lys
        115                 120                 125
Thr Tyr Thr Met Met Gly Ala Asp Val Ser Ala Leu Ser Gly Glu Gly
    130                 135                 140
Asn Gly Val Thr Pro Arg Ile Cys Leu Glu Ile Phe Ala Arg Lys Ala
```

-continued

```
            145                 150                 155                 160
Ser Val Glu Ala Gln Gly His Ser Arg Trp Ile Val Glu Leu Gly Tyr
                    165                 170                 175
Val Glu Val Tyr Asn Glu Arg Val Ser Asp Leu Leu Gly Lys Arg Lys
                180                 185                 190
Lys Gly Val Lys Gly Gly Glu Glu Val Tyr Val Asp Val Arg Glu
            195                 200                 205
His Pro Ser Arg Gly Val Phe Leu Glu Gly Gln Arg Leu Val Glu Val
        210                 215                 220
Gly Ser Leu Asp Asp Val Val Arg Leu Glu Ile Gly Asn Gly Val
225                 230                 235                 240
Arg His Thr Ala Ser Thr Lys Met Asn Asp Arg Ser Ser Arg Ser His
                245                 250                 255
Ala Ile Ile Met Leu Leu Leu Arg Glu Glu Arg Thr Met Thr Thr Lys
                260                 265                 270
Ser Gly Glu Thr Ile Arg Thr Ala Gly Lys Ser Ser Arg Met Asn Leu
            275                 280                 285
Val Asp Leu Ala Gly Ser Glu Arg Val Ala Gln Ser Gln Val Glu Gly
        290                 295                 300
Gln Gln Phe Lys Glu Ala Thr His Ile Asn Leu Ser Leu Thr Thr Leu
305                 310                 315                 320
Gly Arg Val Ile Asp Val Leu Ala Asp Met Ala Thr Lys Gly Ala Lys
                325                 330                 335
Ala Gln Tyr Ser Val Ala Pro Phe Arg Asp Ser Lys Leu Thr Phe Ile
            340                 345                 350
Leu Lys Asp Ser Leu Gly Gly Asn Ser Lys Thr Phe Met Ile Ala Thr
        355                 360                 365
Val Ser Pro Ser Ala Leu Asn Tyr Glu Glu Thr Leu Ser Thr Leu Arg
    370                 375                 380
Tyr Ala Ser Arg Ala Arg Asp Ile Val Asn Val Ala Gln Val Asn Glu
385                 390                 395                 400
Asp Pro Arg Ala Arg Arg Ile Arg Glu Leu Glu Glu Gln Met Glu Asp
                405                 410                 415
Met Arg Gln Ala Met Ala Gly Gly Asp Pro Ala Tyr Val Ser Glu Leu
            420                 425                 430
Lys Lys Lys Leu Ala Leu Leu Glu Ser Glu Ala Gln Lys Arg Ala Ala
        435                 440                 445
Asp Leu Gln Ala Leu Glu Arg Glu His Asn Gln Val Gln Glu
    450                 455                 460
Arg Leu Leu Arg Ala Thr Glu Ala Glu Lys Ser Glu Leu Glu Ser Arg
465                 470                 475                 480
Ala Ala Ala Leu Gln Glu Glu Met Thr Ala Thr Arg Arg Gln Ala Asp
                485                 490                 495
Lys Met Gln Ala Leu Asn Leu Arg Leu Lys Glu Gln Ala Arg Lys
            500                 505                 510
Glu Arg Glu Leu Leu Lys Glu Met Ala Lys Lys Asp Ala Ala Leu Ser
        515                 520                 525
Lys Val Arg Arg Arg Leu Asp Ala Glu Ile Ala Ser Glu Arg Glu Lys
    530                 535                 540
Leu Glu Ser Thr Val Ala Gln Leu Glu Arg Glu Gln Arg Glu Arg Glu
545                 550                 555                 560
Val Ala Leu Asp Ala Leu Gln Thr His Gln Arg Lys Leu Gln Glu Ala
                565                 570                 575
```

```
Leu Glu Ser Ser Glu Arg Thr Ala Ala Glu Arg Asp Gln Leu Leu Gln
                580                 585                 590

Gln Leu Thr Glu Leu Gln Ser Glu Arg Thr Gln Leu Ser Gln Val Val
            595                 600                 605

Thr Asp Arg Glu Arg Leu Thr Arg Asp Leu Gln Arg Ile Gln Tyr Glu
610                 615                 620

Tyr Gly Glu Thr Glu Leu Ala Arg Asp Val Ala Leu Cys Ala Ala Gln
625                 630                 635                 640

Glu Met Glu Ala Arg Tyr His Ala Ala Val Phe His Leu Gln Thr Leu
                645                 650                 655

Leu Glu Leu Ala Thr Glu Trp Glu Asp Ala Leu Arg Glu Arg Ala Leu
            660                 665                 670

Ala Glu Arg Asp Glu Ala Ala Ala Glu Leu Asp Ala Ala Ser
                675                 680                 685

Thr Ser Gln Asn Ala Arg Glu Ser Ala Cys Glu Arg Leu Thr Ser Leu
        690                 695                 700

Glu Gln Gln Leu Arg Glu Ser Glu Glu Arg Ala Ala Glu Leu Ala Ser
705                 710                 715                 720

Gln Leu Glu Ala Thr Ala Ala Lys Ser Ser Ala Glu Gln Asp Arg
                725                 730                 735

Glu Asn Thr Arg Ala Thr Leu Glu Gln Gln Leu Arg Glu Ser Glu Ala
            740                 745                 750

Arg Ala Ala Glu Leu Ala Ser Gln Leu Glu Ala Thr Ala Ala Lys
                755                 760                 765

Met Ser Ala Glu Gln Asp Arg Glu Asn Thr Arg Ala Thr Leu Glu Gln
        770                 775                 780

Gln Leu Arg Asp Ser Glu Glu Arg Ala Ala Glu Leu Ala Ser Gln Leu
785                 790                 795                 800

Glu Ser Thr Thr Ala Ala Lys Met Ser Ala Glu Gln Asp Arg Glu Ser
                805                 810                 815

Thr Arg Ala Thr Leu Glu Gln Gln Leu Arg Asp Ser Glu Glu Arg Ala
            820                 825                 830

Ala Glu Leu Ala Ser Gln Leu Glu Ser Thr Thr Ala Ala Lys Met Ser
        835                 840                 845

Ala Glu Gln Asp Arg Glu Ser Thr Arg Ala Thr Leu Glu Gln Gln Leu
        850                 855                 860

Arg Glu Ser Glu Glu Arg Ala Ala Glu Leu Ala Ser Gln Leu Glu Ser
865                 870                 875                 880

Thr Thr Ala Ala Lys Met Ser Ala Glu Gln Asp Arg Glu Ser Thr Arg
                885                 890                 895

Ala Thr Leu Glu Gln Gln Leu Arg Asp Ser Glu Glu Arg Ala Ala Glu
            900                 905                 910

Leu Ala Ser Gln Leu Glu Ala Thr Ala Ala Lys Ser Ser Ala Glu
        915                 920                 925

Gln Asp Arg Glu Asn Thr Arg Ala Ala Leu Glu Gln Gln Leu Arg Asp
        930                 935                 940

Ser Glu Glu Arg Ala Ala Glu Leu Ala Ser Gln
945                 950                 955

<210> SEQ ID NO 14
<211> LENGTH: 600
<212> TYPE: DNA
<213> ORGANISM: L. chagasi
```

-continued

```
<400> SEQUENCE: 14
gagcagcagc ttcgcgaatc cgaggcgcgc gctgcggagc tggcgagcca gctggaggcc      60
actgctgctg cgaagatgtc agcggagcag gaccgcgaga acacgagggc cacgctagag     120
cagcagcttc gtgactccga ggagcgcgct gcggagctgg cgagccagct ggagtccact     180
actgctgcga agatgtcagc ggagcaggac cgcgagagca cgagggccac gctagagcag     240
cagcttcgtg actccgagga gcgcgctgcg gagctggcga ccagctgga gtccactact     300 gctgcgaaga tgtcagcgga gcaggaccgc gagagcacga gggccacgct agagcagcag     360
cttcgcgaat ccgaggagcg cgctgcggag ctggcgagcc agctggagtc cactactgct     420
gcgaagatgt cagcggagca ggaccgcgag agcacgaggg ccacgctaga gcagcagctt     480
cgtgactccg aggagcgcgc tgcggagctg gcgagccagc tggaggccac tgctgctgcg     540
aagtcgtcgg cggagcagga ccgcgagaac acgagggccg cgttggagca gcagcttcgt     600

<210> SEQ ID NO 15
<211> LENGTH: 561
<212> TYPE: DNA
<213> ORGANISM: L. donovani

<400> SEQUENCE: 15
gagcagcagc ttcgtgaatc cgaggcgcgc gctgcggagc tgaaagccga gctggaggcc      60
actgctgctg cgaagacgtc ggtggagcag gagcgtgaga agacgaggac ggctctggag     120
gggcgcgctg cggagctggc tcgcaaactg gaggcgactg cttctgcgaa gaatttggta     180
gagcaggacc gcgagaggac gagggccacc ttggaggaac gacttcgtat tgctgaggtg     240
cgcgctgcgg agctggcagg agtgctggag gccactgctg ctgcgaagac ggcggtggag     300
caggagcgtg agaggacgag ggccgccttg agcagcagc tccgcgaatc cgaggcgcgc     360
gctgcggagc tggctgcgca gctggaagcc gctgctgcgg cgaagacgtc ggtggagcag     420
gagcgtgaga acacgagggc caccttggag gagcggttgc ggctcgctga ggtccgcgct     480
gcggagctgg cagcgcggct aaagagcact gctgctgtta agtccgcgat ggagcaggac     540
cgcgagaaca cgagggccac g                                              561

<210> SEQ ID NO 16
<211> LENGTH: 240
<212> TYPE: PRT
<213> ORGANISM: L. chagasi

<400> SEQUENCE: 16

Leu Glu Gln Gln Leu Arg Glu Ser Glu Glu Arg Ala Ala Glu Leu Ala
1               5                   10                  15

Ser Gln Leu Glu Ala Thr Ala Ala Lys Ser Ser Ala Glu Gln Asp
            20                  25                  30

Arg Glu Asn Thr Arg Ala Thr Leu Glu Gln Gln Leu Arg Glu Ser Glu
        35                  40                  45

Ala Arg Ala Ala Glu Leu Ala Ser Gln Leu Glu Ala Thr Ala Ala Ala
    50                  55                  60

Lys Met Ser Ala Glu Gln Asp Arg Glu Asn Thr Arg Ala Thr Leu Glu
65                  70                  75                  80

Gln Gln Leu Arg Asp Ser Glu Glu Arg Ala Ala Glu Leu Ala Ser Gln
                85                  90                  95

Leu Glu Ser Thr Thr Ala Ala Lys Met Ser Ala Glu Gln Asp Arg Glu
            100                 105                 110
```

-continued

```
Ser Thr Arg Ala Thr Leu Glu Gln Gln Leu Arg Asp Ser Glu Glu Arg
        115                 120                 125

Ala Ala Glu Leu Ala Ser Gln Leu Glu Ser Thr Thr Ala Ala Lys Met
        130                 135                 140

Ser Ala Glu Gln Asp Arg Glu Ser Thr Arg Ala Thr Leu Glu Gln Gln
145                 150                 155                 160

Leu Arg Glu Ser Glu Glu Arg Ala Ala Glu Leu Ala Ser Gln Leu Glu
                165                 170                 175

Ser Thr Thr Ala Ala Lys Met Ser Ala Glu Gln Asp Arg Glu Ser Thr
                180                 185                 190

Arg Ala Thr Leu Glu Gln Gln Leu Arg Asp Ser Glu Glu Arg Ala Ala
        195                 200                 205

Glu Leu Ala Ser Gln Leu Glu Ala Thr Ala Ala Ala Lys Ser Ser Ala
        210                 215                 220

Glu Gln Asp Arg Glu Asn Thr Arg Ala Ala Leu Glu Gln Gln Leu Arg
225                 230                 235                 240
```

US 7,740,859 B2

POLYPEPTIDES FOR THE DIAGNOSIS AND THERAPY OF LEISHAMANIASIS

TECHNICAL FIELD

The present invention relates to compounds and methods for the detection of anti-leishmanial antibodies in individuals suspected of infection with the protozoan parasite of the genus *Leishmania* especially the infectious agent is an Indian strain and similar or closely related to Indian *Leishmania* strains. Further, the present invention provides a diagnostic kit consisting of the polypeptide as shown in SEQ ID NO: 5 or SEQ ID NO: 6 for the detection of anti-leishmanial antibodies in individuals where the immune responses are elicited against species of Indian strains and similar or closely related to Indian *Leishmania* strains, and also useful as a vaccine and therapeutic agent to prevent and treat leishmaniasis. The present invention further provides a diagnostic kit consisting of antibody raised against polypeptides as shown in SEQ ID NO: 5 or SEQ ID NO: 6 for detecting leishmanial antigens

BACKGROUND OF THE INVENTION

Leishmaniasis, a vector-borne parasitic disease, is caused by obligate intramacrophage protozoa. It is characterized by diversity and complexity. It presents itself with a wide range of clinical forms. However, there are mainly 4 clinical forms. The Visceral Leishmaniasis (VL), also known as kala azar, is the most severe form of the disease, which, if untreated, has a mortality rate of almost 100%. The Cutaneous Leishmaniasis (CL) produces skin ulcers on the exposed parts of the body, such as the face, arms and legs. The number of ulcers may vary from 1 to as many as 200 in some cases, causing serious disability and leaving the patient permanently scarred. The third form is Mucocutaneous Leishmaniasis (MCL), or espundia. It can lead to extensive and disfiguring destruction of mucous membranes of the nose, mouth and throat cavities and can involve even the cartilage. The cutaneous form may lead to disseminated form, known as Diffuse Cutaneous Leishmaniasis (DCL). Leishmaniasis is caused by a total of about 21 species, which are transmitted by about 30 species of phlebotomine sandflies [Herwaldt B L., 1999].

The leishmaniasis are presently endemic in 88 countries on five continents, Africa, Asia, Europe, North America and South America, and a total of 350 million people are at risk of infection. It is estimated that worldwide 12 million people are affected by leishmaniasis; this figure includes cases with overt disease and those with no apparent symptoms. Of the 1.5-2 million new cases estimated to occur annually, only 600 000 are officially declared. Of the 500 000 new cases of VL, which occur annually, 90%, are in five developing countries: Bangladesh, Brazil, India, Nepal and Sudan. About 90% of all cases of MCL occur in Bolivia, Brazil and Peru and 90% of all cases of CL occur in Afghanistan, Brazil, Iran, Peru, Saudi Arabia and Syria, with 1-1.5 million new cases reported annually worldwide. The geographical distribution of leishmaniasis is limited by the distribution of the sandfly, its susceptibility to cold climates, its tendency to take blood from humans or animals only and its capacity to support the internal development of specific species of *Leishmania* [Desjeux P 2001].

Since 1993, regions that are *Leishmania*-endemic have expanded significantly, accompanied by a sharp increase in the number of recorded cases of the disease. The geographic spread is due to factors related mostly to development. These include massive rural-urban migration and agro-industrial projects that bring non-immune urban dwellers into endemic rural areas. Man-made projects with environmental impact, like dams, irrigation systems and wells, as well as deforestation, also contribute to the spread of leishmaniasis. AIDS and other immunosuppressive conditions increase the risk of *Leishmania*-infected people developing visceral illness [Desjeux P 2001, Paredes R et al., 1997].

VL is primarily caused by *L. donovani* in the Indian subcontinent and Africa, *Leishmania infantum* in Mediterranean region and *Leishmania chagasi* in the new world; of these species *Leishmania chagasi* and *Leishmania infantum* are closely related. Although, all the above species cause VL they are genetically different from each other. The data obtained by Cupolillo E et al., [1994] using numerical zymotaxonomy showed that *L. chagasi*, the new world visceralising species is similar to the old world *L. infantum*. The Zymodeme, serodeme, quantitative comparisons of nuclear DNA fragment patterns all indicates that *L. chagasi* and *L. Infantum* are closely related and may represent the same species. Also, the study by Beverley S. M. et al., [1987] based on nuclear DNA restriction fragment patterns reveals that, the *L. chagasi* and *L. infantum* are similar and as closely related to each other as two random individuals from the same population and *L. donovani* is different from these two species. In another study using analysis of repetitive DNA sequence by Piarroux R et al., [1995] it was observed that, amongst the *leishmania* causing VL, *L. donovani* isolated from foci in which human beings are the main reservoirs clustered in an independent branch and by contrast, *L. infantum* and *L. chagasi* are canine parasites that rarely infect human beings and thus are different. A recent study by Mauricio I. L et al., [1999] using three different approaches at different levels of resolution to explore the genetic information from *leishmania* species reveals a substantial amount of diversity within *L. donovani* complex. Further, RAPD had grouped *L. donovani* strains according to the geographical origins, specifically Indian and Kenyan, showing a substantial divergence within taxon.

Genetic diversity is not only common for *L. donovani*, even in *L. major* which causes cutaneous leishmaniasis, strains isolated from the same geographical area show minor chromosomal size polymorphisms in their molecular karyotypes whereas strains from different geographical areas show more significant differences suggesting that the genomes of species of *leishmania* are quite plastic and that chromosomal rearrangements occurs during the evolution of various species [Samaras N et al., 1987]. Currently a WHO sponsored genome mapping project on *L. major* is underway. Although it has been argued that the genome map of one strain would be applicable to another, there is very little evidence to substantiate this claim. Indeed, it is known that differences in gene copy number and organization differ between *L. donovani*, *L. chagasi*, *L. major* and other species. Moreover, it is difficult to reconcile the great differences in clinical symptoms caused by different species with identical genotype [Ghosh S. S., et al., 1998]. For these reasons, it is necessary to characterize important genes, which have potential to be a diagnostic or vaccine or therapeutic candidate from different geographical regions. The assignment of the parasite species based alone on geographic location or the site of infection is not satisfactory. Accordingly, correct diagnosis and classification of pathogenic *Leishmania* isolate is essential to determine the clinical prognosis and a species-specific therapeutic approach [Marfurt J., et al., 2003]. One such potential gene studied widely across different species from different geographical region is Gp63 a glycolipid-anchored zinc protease of 63 kDa size [Webb J. R., et al., 1991; Steinkraus H B et al., 1993; Roberts S C et al., 1993].

In India, VL is a serious problem in Bihar, west Bengal and eastern Uttar Pradesh where, there is under-reporting of kala-azar (KA) and post kala-azar dermal leishmaniasis in women and children of 0-9 years of age. The recent epidemics in 1992 of VL killed more than 100,000 people in India and Sudan. Spraying of DDT helped control KA in India, however there are reports of the vector phlebotomus argentipes developing resistance. Also, lymphadenopathy, a major presenting feature in India raises the possibility of a new vector or a variant of the disease [Bora D., 1999].

The Post kala-azar dermal leishmaniasis (PKDL) is a sequel to KA in India and Sudan; the disease develops months to years after the patient recovery from KA. Cutaneous lesions characterize the disease and they demonstrate great variability, ranging from hypo-pigmented macules to erythematous papules and from nodules to plaques. As in leprosy, the wide clinical spectrum of PKDL reflects the immune response of the individual to the *leishmania* organism. Lesions may be numerous and persist for decades. Isolated parasites from the lesions are identical to those causing the original visceral disease.

The clinical and epidemiological findings in *leishmaniases* are not pathognomic and these can mimic with several endemic conditions such as malaria, tuberculosis, syphilis and fungal infections. Hence a laboratory diagnosis is required to confirm the clinical suspicion. The diagnostic tools used for each leishmanial syndrome viz. visceral, cutaneous, and mucocutaneous form, vary but the gold standard in each case remains the demonstration and isolation of the parasite from appropriate tissue [Singh S et al., 2003].

The clinical signs and symptoms are not enough to differentiate VL from other similar conditions such as malaria, tropical splenomegaly syndrome schistosomiasis or cirrhosis with portal hypertension, African trypanosomiasis, milliary tuberculosis, brucellosis, typhoid fever, bacterial endocarditis, histoplasmosis, malnutrition, lymphoma, and leukemia. Hence other diagnostic methods are required [Herwaldt B L, 1999; Davidson R N, 1998]. Amongst these the most specific and standard technique is parasitological demonstration or isolation of the causative agent. Marrow obtained from sternal or iliac crest puncture is a much safer but a painful method. The aspirates are smeared on the glass slide and stained with Romanowsky's stain to demonstrate the amastigote forms of the parasite. However; on culture it can give positive results in up to 80% of the cases. Lymph gland puncture gives positive results in 60% of the cases. Juice is extracted from any enlarged lymph gland and subjected to both direct examination and culture to give the best chance of diagnosis [Williams, J. E, 1995; Manson-Bahr PEC, 1987]. Primary isolation of *L. donovani* is made on solid Novy-MacNeal-Nicolle (NNN) medium having 20-30% rabbit blood or liquid Schneider's insect medium supplemented with 10% v/v foetal calf serum (FCS). Other suitable growth media can also be used particularly for maintaining the sub-cultures of the promastigotes using FCS or other supplements including human urine [Singh S et al., 2000]. Demonstration of the parasites in the spleen and liver is one of the most accurate methods available to determine leishmanial infections. Ninety percent of the active cases show parasites in splenic and liver aspirates. The smallest needle possible, preferably, 21-gauge (0.8 mm) should be used to minimize the risk of complications such as hemorrhage of the spleen [Williams, J. E, 1995]. Part of the splenic aspirate can be used to make smears for direct microscopic examination and the rest should be cultured. Liver biopsy material is less likely to demonstrate parasites on direct examination or on culture; however histological examination will show amastigotes in Kupffer cells in the portal system.

Occasional reports of finding the *Leishmania* parasites in blood in patients of Kala-azar from Kenya and India have been published. Blood in anticoagulant is centrifuged at 2000 g for 10 min and the cells from the buffy coat removed and used to prepare smears and inoculate cultures. The amastigotes can be found in and around Macrophage cells. The volume used in culture inoculation is important, 1-3 drops on NNN or Schneider's medium has given successful results [Manson-Bahr PEC, 1987].

The conventional microscopic methods are invasive and painful carrying risk of iatrogenic infections and fatal hemorrhages. Though demonstration of the amastigote form of parasite in the tissues is being used since its discovery as a parasitic disease in 1903, it is least sensitive and unable to detect occult and sub clinical infections. The sub clinical and latent form of infection has become a major concern in recent years, as these can flare up due to immune suppression such as in HIV infection and the infection can be transmitted through organ transplants. Serological diagnosis is based on the presence of specific humoral response as in cases of visceral leishmaniasis or cell mediated immune response in cases of cutaneous and mucocutaneous leishmaniasis, evoked by the immune system against the causative pathogen. There are ranges of serological methods available for the diagnosis of VL varying in accuracy and specificity. These included non-specific and specific tests. With on-going research newer better methods are continually becoming available.

The formol gel test is oldest serological test and has the advantage of being cheap and simple to perform. Serum obtained from about 5 ml of blood is mixed with one drop of 30% formaldehyde. A positive reaction is shown if the mixture solidifies and forms a white opaque precipitate within 20 minutes. A positive test cannot be detected until 3 months after infection and becomes negative 6 months after cure. The test is non-specific since it is based on detecting raised levels of IgG and IgM immunoglobulins which are also raised in other infections such as African trypanosomiasis, malaria and schistosomiasis etc., [WHO expert committee report, 1991]. Several other tests based on this principle had been in use in past but very rarely used these days [Singh S, 1999].

There are number of specific serological tests and all have variable sensitivity and specificity for disease diagnosis. Some of these tests include indirect haemagglutination (IHA), counter current immunoelectrophoresis (CCIEP), Immunodiffusion (ID) etc. but all these tests are cumbersome and lack sensitivity and specificity and hence not commonly used. Some more commonly used ones are described below.

1. Leishmanin Skin Test (LST): Delayed hypersensitivity is an important feature of cutaneous forms of human leishmaniasis and can be measured by the leishmanin test, also known as the Montenegro reaction. Leishmanin is a killed suspension of whole ($0.5-1 \times 10^7$/ml) or disrupted (250 µg protein/ml) promastigotes in pyrogen-free phenol saline. No cross-reactions occur with chagas disease, but some cross-reactions are found with cases of glandular tuberculosis and lepromatous leprosy. Leishmanin Skin Test is usually used as an indicator of the prevalence of cutaneous and mucocutaneous Leishmaniasis in human and animal populations and successful cure of the visceral leishmaniasis [Singh S, 1999, Sassi A, et al., 1999]. During active kala-azar disease there will be no or negligible cell mediated immune response. However, the leishmanin antigen is not commercially available and no field study has been carried out in India.

2. Indirect fluorescent antibody test (IFAT): The Indirect fluorescent antibody test is one of the most sensitive tests available. The test is based on detecting antibodies, which are demonstrated in the very early stages of infection and undetectable six to nine months after cure. If the antibodies persist in low titers it is good indication of a probable relapse. Titers above 1/20 are significant and above 1/128 are diagnostic [Williams, J. E, 1995]. There is a possibility of a cross reaction with trypanosomal sera, however, this can be overcome by using *leishmania* amastigotes as the antigen instead of the promastigotes [Gari-Toussaint M, et al., 1994].

3. Agglutination test: The DAT is a highly specific and sensitive test. It is cheap and simple to perform making it ideal for both field and laboratory use. The antigen is prepared from promastigotes of *L. donovani* and test can be carried out on plasma, serum, blood spots and whole blood. For long time DAT remained first line diagnostic tool in resource poor countries. The method uses whole, stained promastigotes either as a suspension or in a freeze-dried form. The freeze-dried form is heat stable and facilitates the use of DAT in the field. However, the major disadvantage of DAT is the relative long incubation time of 18 h and the need for serial dilutions of blood or serum [Schallig H D et al., 2001]. Another major disadvantage of DAT is that it has no prognostic value for evaluating the parasitological cure of the disease, as the test may remain positive for several years after cure. Recently, Schoone et al [2001] have developed a fast agglutination-screening test for the rapid detection (<3 h) of anti-*leishmania* antibodies in serum samples and on blood collected on filter paper. The FAST utilizes only one serum dilution leading to qualitative results. The FAST offers the advantages of the DAT based on the freeze-dried antigen with respect to stability of the antigen, reproducibility, specificity and sensitivity.

4. Immunoblotting: Serodiagnosis using immunoblotting has been attempted and reported superior and stage specific. The various antigens expressed during the course of infection can also be documented. It also has an added advantage of permanent documentation. However, the technique is not user friendly and limited only to research laboratories [Herwaldt B L., 1999; Singh S, 1999; Schallig H D et al., 2001].

5. Antigen Detection: The detection of antigen in the patient's serum is complicated by the presence of high level of antibodies, circulating immune complexes, serum amyloid, rheumatoid factor and auto antibodies all of which may mask immunologically important antigenic determinants or competitively inhibit the binding of free antigen. Antigen detection test would, in principle provide better means of diagnosis of leishmaniasis. Since antigen levels are expected to broadly correlate with the parasite load, the antigen detection may be an ideal alternative to the antibody detection in immunocompromised patients, where antibody response is very poor. Though a few reports are published, no satisfactory antigen detection system is currently available [Senaldi G et al., 2001; Attar Z J et al., 2001]. Recently, a latex agglutination test (KATEX) for the detection of leishmanial antigens in the urine of patients with VL is developed. The results obtained with KATEX using samples collected from different foci of VL indicate that, the test works well regardless of the geographical origin of samples. The test had 100% specificity and sensitivity between 68-100% [Attar Z J et al., 2001]. Whether the test has applications for the detection of asymptomatic cases of VL and monitoring therapy is yet to be confirmed.

6. Enzyme linked immunosorbent assay (ELISA): The Enzyme Linked Immunosorbant Assay (ELISA) is a valuable tool in the serodiagnosis of leishmaniasis. The test is useful for laboratory analysis or field applications. The ELISA can be performed easily and is adaptable for use with purified or defined antigen. The antigens used in the design of immunodiagnostic tests for leishmaniasis have traditionally been derived from promastigotes that have been cultivated in vitro or from recombinant proteins, alteration of the antigen used for ELISA and DAT from the whole promastigote or soluble antigens to more specific and potential recombinant leishmanial and peptide antigens have improved VL diagnosis [Senaldi G et al., 2001]. Immunodiagnosis is greatly influenced by the antigen used. Several antigen molecules have recently been reported [Martin S K et al., 1998; Rajasekariah G H et al., 2001]. The excretory, secretary and metabolic antigens (Ld-ESM), released by *L. donovani* promastigotes into a protein-free medium were used for the serodiagnosis of VL by ELISA. The Ld-ESM has been found to be 100% specific and sensitive, the Positive Predictive Value was 99.99% and Negative Predictive Value was 95.45%. However further retrospective and prospective multisite evaluation is required to validate these findings [Schoone G J et al., 2001]. Lately, a variety of recombinant antigens have been developed, recently a gene related to the *L. major* gene B encoding a hydrophilic protein expressed on the surface of both promastigotes and amastigotes of *L. major* characterized by an amino acid repeating motif of 5.5 copies of a 14-amino acid sequence has been identified and shown to be expressed in *L. donovani*. The protein encoded by *L. donovani* gene B homologue contains up to 22 copies of a repetitive element in which 9 out of 14 residues are completely conserved between the two species. An ELISA using repetitive peptide sequence from *L. donovani* GBP and recombinant *L. donovani* GBP as solid-phase ligand was developed. However the limitations of this antigen are that it can be used for serodiagnosis of visceral leishmaniasis only in areas endemic for *L. donovani* but not for areas that are co-endemic for other *Leishmania* species and the specificity and sensitivity are not very high [Jensen A T et al 1999].

Raj et al., [1999] have developed another recombinant protein rORFF of *L. infantum* origin for diagnosis of VL in India. The ORFF protein is encoded in the LD1 locus of chromosome 35 of *L. infantum*, an ELISA with this antigen proved to be sensitive with as little as 5 ng of rORFF when performed with different groups of patients like confirmed VL, suspected VL, Intermittently treated endemic normal and non-endemic normal controls. Further the same patient groups were subjected to DAT using whole promastigote and ELISA using total soluble antigens. The ELISA using rORFF was found to be more sensitive than others. Although this antigen is highly sensitive (95 to 100%) and specific (>90%) for VL, it also was found to be positive in 40% cases of confirmed CL due to *L. major* or *L. tropica*. Further the test needs to be evaluated by others and its utility for the field diagnosis is yet to be studied. In a recent study conducted in Mediterranean VL where *L. infantum* is the causative agent, ten recombinant and purified *leismania* antigens have been compared using ELISA method by Maalej et al., [2003]. Of these recombinant antigens rgp63, a major surface antigen of *leishmania* which is not present on *Trypanosoma cruzi* or other kinetoplastids and rGBP had good performance but not very sensitive and specific for reliable diagnosis. It is suggested that the use of recombinant proteins from *L. infantum* rather than *L. major* would have yielded a better result.

A recombinant antigen developed by Burns et al., [1993] belonging to the kinesin family of motor proteins, recombinant K39 (rK39) has been shown to be specific for antibodies arising during VL caused by members of the *L. donovani* complex, which include *Leishmania chagasi* and *L. infantum*. This antigen, which is member of the kinesin family, encodes a protein with a repetitive epitope, consisting of 39 amino acid residues (K39) is highly sensitive and predictive of acute disease. The high anti-rK39 antibody titers have been demonstrated in VL patients but it shows no detectable anti-rK39 antibodies in cutaneous or mucocutaneous leishmaniasis. The antibody titers to this antigen directly correlate with active disease and have a tremendous potential as a means of monitoring chemotherapy and in predicting clinical relapse [Burns J M Jr et al., 1993; Singh S et al., 1995; Badaro R et al., 1996; Singh S et al., 2002; Maalej I A et al., 2003; The U.S. Pat. Nos. 5,411,865 and 5,719,263]. In addition rK39 ELISA, has a high predictive value for detecting VL in immunocompromised persons, like AIDS patients [Houghton R L et al., 1998]. This antigen is now commercially available in the form of antigen-impregnated nitrocellulose paper strips adapted for use under field conditions. The rK39 strip test has been found useful for the field diagnosis of kala-azar in India [Sundar S et al., 1998] however the same had markedly less sensitivity in Sudan [Zijlstra E E et al., 2001] and southern Europe. It is important to emphasize here that though the kinesin related antigen gene has been shown to be conserved in all visceralising species, but the same seems not to be case, because *L. donovani* is the causative agent of kala-azar in India as well as in Sudan, and in both the geographical regions they cause PKDL as a sequel to VL. But the observations of Zijlstra et al., [2001] that, the rK39 strip tests are less sensitive (only upto 67%) in Sudan and even in Southern Europe (only upto 71.4%) [Jelinek T et al., 1999] raise the valid doubt about the universal suitability of this antigen. One explanation often given for this variable sensitivity is that may be the antibody response elicited by different ethnic groups differs remarkably [Sundar S et al., 2002]. Alternatively, it could also be possible that, the antigenic gene itself varies notably from strain to strain and also in different geographical regions or a variant of this antigen exist and evades immune elucidation as a result the disease goes undetected in few cases when the existing rK39 from *L. chagasi* is used for the diagnosis. Further, of the 500,000 new case of VL, which occurs annually worldwide, more than 90% of are reported from India, Bangladesh, Southern Sudan, and northeast Brazil [Sundar S et al., 2002].

India harbors majority of VL cases in the world, and the kinesin related antigen was not yet characterized from the Indian isolates of *Leishmania donovani*. It is also evident that, *L. chagasi* has the animal reservoir while the *L. donovani* does not. It is possible that, the gene differs significantly from the *L. chagasi* and the characterization of this gene will also explain reasons for the poor sensitivity of rK39 strip test in certain geographical regions. In an attempt to solve this problem, we have cloned and characterized the kinesin gene from different strains isolated from two individuals infected by *L. donovani* belonging to the same geographical region in India. One strain MHOM/IN/DD8 was the well characterized WHO reference strain for India isolated in 1980 and the second strain MHOM/IN/KE16/1998 is a recent clinical isolate from a 10 year old female Kala-azar patient from Muzaffarpur, Bihar, India. This clearly explains that, it is the variation at the gene level that may have caused reduced sensitivity in certain geographical regions. Had this kinesin gene not been characterized from Indian isolates, this information of variation at the gene level never would have become known to the scientific community. This is evident from the ELISA results, as the mean titers for the antigen from MHOM/IN/DD8 is considerably lower than for the one of MHOM/IN/KE16/1998 and *L. chagasi* rK 39.

The applicants did extensive search of the US patent database with different key words to study the previous work done on the K39 immunodominant repeat antigen and 230 kD antigen. Discussed below are the few US patents by Reed on the subject concerned and the uniqueness of the applicant's antigen.

The U.S. Pat. No. 5,411,865 by Reed in May 2, 1995 teaches about the method of detecting anti-*leishmania* parasite antibodies. The compound disclosed a method for detecting anti-*Leishmania* parasite antibodies to a 230 kDa antigen present in *Leishmania chagasi* and *Leishmania donovani* which comprises obtaining a sample from an individual, contacting the sample with a recombinant K39 repeat regionantigen comprising the amino acid sequence as shown in SEQ ID NO: 3, and detecting the presence of anti-*Leishmania* parasite antibodies in the sample which bind to the recombinant K39 repeat regionantigen.

The U.S. Pat. No. 5,719,263 by Reed in Feb. 17, 1998 teaches about the 230 Kd antigen present in *Leishmania* species. The compound disclosed is an isolated 230 kD antigen that is present in *Leishmania chagasi* and *Leishmania donovani*, and isolated polypeptides comprising one or a plurality of K39 repeat antigens. Also disclosed are DNAs encoding the 230 kD antigen and the K39 repeat antigen, and vaccine compositions comprising the antigens.

The above disclosed 230 kDa antigen and the isolated polypeptide comprising the K39 repeats are reported to be not sensitive in certain geographical areas where VL is highly endemic and caused by *L. donovani*. However, it should be noted that, the K39 repeats has been characterized only from *L. chagasi* and not from *L. donovani*. The major burden in leishmaniasis throughout the world is caused by *L. donovani*. It is also evident from the reports that, the two species are genetically different. Hence, the applicants cloned and characterized K39 repeat immunodominant region from the Indian isolates of *Leishmania donovani*, which contributes significantly to the global VL burden.

The applicant's present invention discloses a 29 kDa and 26 kDa repeat antigen, which is present in *leishmania* species. The compounds disclosed are an isolated 29 kD and 26 kD antigens, which are characterized from the Indian isolates of *Leishmania donovani*. The reported antigens are entirely different from the *Leishmania chagasi* 230 kDa antigen. The antigen varies significantly, more than 60% in its predicted amino acid sequence to that of K39 repeat antigen from *L. chagasi*. Also disclosed are DNA encoding the 29 kD and 26 kD) antigen and therapeutic and vaccine compositions comprising the antigens.

The U.S. Pat. No. 5,912,166 by Reed, et al., in Jun. 15, 1999 teaches about compounds and methods for diagnosis of leishmaniasis infection. The compounds provided include polypeptides that contain at least an epitope of the *Leishmania chagasi* acidic ribosomal antigen LcP0, or a variant thereof. Such compounds are useful in a variety of immunoassays for detecting *Leishmania* infection and for identifying individuals with asymptomatic infections that are likely to progress to acute visceral leishmaniasis. The polypeptide compounds are further useful in vaccines and pharmaceutical compositions for preventing leishmaniasis.

However, the applicant's present invention does not deal with acidic ribosomal antigen LcPO.

The U.S. Pat. No. 6,638,517 by Reed, et al., in Oct. 28, 2003, *Leishmania* antigens for use in the therapy and diagnosis of leishmaniasis teaches compositions and methods for preventing, treating and detecting leishmaniasis and stimulating immune responses in patients. The compounds provided include polypeptides that contain an immunogenic portion of one or more *Leishmania* antigens, or a variant thereof. The patent also discloses vaccines and pharmaceutical compositions comprising such polypeptides, or polynucleotides encoding such polypeptides, are also provided and may be used, for example, for the prevention and therapy of leishmaniasis, as well as for the detection of *Leishmania* infection.

The compounds provided in the above patent utilize a sequence of *L. major* origin and a fusion construct from multiple *leishmania* antigens. These compounds are in no way similar to the applicant's antigen The kinesin related antigen gene has been cloned and characterized from *L. chagasi* an South American visceralising species by Burns et al., [1993], this led to the development of rK39 antigen, a recombinant protein with 39 amino acid tandem repeats. This antigen from a new world visceralising species *L. chagasi* is reported not sensitive in some highly endemic regions for VL, Sudan and Southern Europe as it is on some other geographical areas, India, Bangladesh, Nepal etc., [Sundar et al., 2002] India carries the majority of the VL population in the global leishmaniasis burden. So, it is very important to have precise and well characterized tools for the diagnosis and other control measures. The applicants have characterized the kinesin related antigen at the sequence level to study, whether the sequence is similar to that of *L. chagasi* which is well characterized and to rule out the possibility of some VL and PKDL cases going undetected in India as those reported in Sudan. This study will also through light on the reasons for the varied response among the ethnic groups, which harbor this disease to the rK39 antigen of Burns et al., [1993]. In the present invention we found that, the sequence of our kinesin antigen significantly differs from that of the published reports of *L. chagasi* from which the rK39 of Burns et al, was derived. This invention also provides a method for detection of anti-leishmanial antibodies using the antigens derived from the Indian isolates of *L. donovani.*

The study was important to analyze the response to the antigen in the various ethnic groups in India. It is possible that the antibody levels in the diseased people of India may be due to either the strains being different or it is possible that the various ethnic groups respond to the *Leishmania* antigen in different manner.

OBJECTS OF THE INVENTION

The main object of this invention is to isolate, characterize and use the immunodominant region of the kinesin related antigen gene from Indian isolate of *Leishmania donovani* strain MHOM/IN/DD8, Another object of this invention is to isolate, characterize and use the immunodominant region of the kinesin related antigen gene from Indian isolate of *Leishmania donovani* strain MHOM/IN/KE16/1998, Another object of this invention is to identify and do comparative sequence analysis both at nucleic acid and amino acid level of the Indian isolates with that of the *L. chagasi* kinesin immunodominant region, Still another object is to identify the variations in the 39 amino acid immunodominant repeat region of the kinesin gene isolated from the Indian strains as compared to other reported sequences, Still another object is to produce polypeptide containing one or more 39 amino acid repeat region from the Indian strains, Still another object is to produce recombinant polypeptide containing one or more 39 amino acids repeat region from the Indian strains.

Another object of this invention is to provide a method of detecting anti- leishmanial antibody from the *leishmania* infected patients using the above said polypeptide.

Another object of this invention is to provide a kit containing the polypeptide from the Indian isolates of *Leishmania donovani* to detect anti leishmanial antibody in VL and PKDL patients.

Still another object of this invention is to produce antibody raised against the polypeptides as shown in SEQ ID NO: 5 or SEQ ID NO: 6.

Still another object of this invention is to provide a method for detection of Leishmanial antigens using the above said antibody.

Still another object of this invention is to provide a diagnostic kit consisting of antibody raised against polypeptides as shown in SEQ ID NO: 5 or SEQ ID NO: 6 for detecting Leishmanial antigens.

SUMMARY OF THE INVENTION

Accordingly, the present invention provides polypeptides identified as SEQ ID NO: 5 and SEQ ID NO: 6, isolated from Indian strains of *Leishmania donovani* for the purpose of detecting anti-leishmanial antibodies from infected samples collected from animals or human beings. The invention also provides an ELISA method for detecting the above infection caused by the protozoan parasite of the genus *Leishmania*. The invention further provides a diagnostic kit for detecting leishmaniasis (VL and PKDL) in blood samples. The present invention further provides a diagnostic kit consisting of antibody raised against polypeptides as shown in SEQ ID NO: 5 or SEQ ID NO: 6 for detecting leishmanial antigens

BRIEF DESCRIPTION OF THE DRAWINGS

FIG. 1:

Cloning of 563 bp PCR product in pGEMTE vector (Promega) from the strain MHOM/IN/DD8. Lane 1: 1 kb Molecular Weight Marker (MBI Fermentas), Lane 2: Eco R1 digested Plasmid with released 563 bp insert, Lane 3: Undigested pGEMTE with Insert, Lane 4: Eco R1 digested Plasmid with released 563 bp insert, Lane 5: Undigested pGEMTE with Insert.

FIG. 2:

Cloning of 466 bp PCR product in pGEMTE vector (Promega) from the strain MHOM/IN/KE16/1998. Lane 1: 1 kb Molecular Weight Marker (MBI Fermentas), Lane 2: Eco R1 digested Plasmid with released 466 bp insert, Lane 3: Undigested pGEMTE with Insert, Lane 4: Eco R1 digested Plasmid with released 466 bp insert, Lane 5: Undigested pGEMTE with Insert.

FIG. 3: The BLAST searches against predicted protein sequence of *L. donovani* strain MHOM/IN/DD8 (SEQ ID NO:5) using patent division of GenBank database. FIG. 3A to 3F, BLAST results against patent database. Query: polypeptide from *L. donovani* strain MHOM/IN/DD8 (SEQ ID NO:5), subject: patented sequences from U.S. Pat. Nos. 5,411,865, 5,719,263, 5,912,166.

FIG. 3A-C shows homology between SEQ ID NO: 5 and SEQ ID NO: 1 from U.S. Pat. No. 5,411,865 which is same as the SEQ ID NO: 2 of U.S. Pat. No. 5,719,263 (SEQ ID NO: 12).

FIG. 3D-F shows homology between SEQ ID NO: 5 and SEQ ID NO: 3 from U.S. Pat. No. 5,912,166 (SEQ ID NO: 13).

FIG. 4: (SEQ ID NOS: 14, 4, and 15, respectively) Clustal W multiple sequence alignment of the immunodominant repeat region at the nucleotide level for the sequences, SEQ ID NO: 15 and SEQ ID NO: 4 with that of the immunodominant repeat region of *L. chagasi*. LCIMM: immunodominant repeat region for the species *L. chagasi* (Gen Bank accession No. L07879); DDIMM (Reverse complementary sequence of SEQ ID NO: 3) immunodominant repeat region for the species *L. donovani* of Indian strain MHOM/IN/DD8; KEIMM: (SEQ ID NO: 4) immunodominant repeat region for the Indian strain MHOM/IN/KE16/1998. [- - -: Represents gaps, identical sequences are shaded black].

FIG. 5: (SEQ ID NOS: 16, 6, and 5, respectively) Clustal W multiple sequence alignment of the immunodominant repeat region at the Amino acid level for the sequences, SEQ ID NO: 5 and SEQ ID NO: 6 with that of the immunodominant repeat region of *L. chagasi*. LCIMM: immunodominant repeat region for the species *L. chagasi*, (Gen Bank accession No. L07879). The sequence DDIMM (SEQ ID NO: 5) is the immunodominant repeat region for the species *L. donovani* of Indian strain MHOM/IN/DD8, and KEIMM (SEQ ID NO: 6) is the immunodominant repeat region for the Indian strain MHOM/IN/KE16/1998.

[- - -: Represents gaps, identical sequences are shaded black and similar sequences are shaded grey].

FIG. 6: (SEQ ID NOS: 16 and 5, respectively) Clustal W multiple sequence alignment of the immunodominant repeat region at the Amino acid level for the SEQ ID NO: 5 (DDIMM) with that of the immunodominant repeat region of *L. chagasi*. LCIMM represents the immunodominant repeat region for the species *L. chagasi* (Gen Bank accession No. L07879).

[- - -: Represents gaps, identical sequences are shaded black and similar sequences are shaded grey].

FIG. 7:

Clustal W multiple sequence alignment of the immunodominant repeat region at the Amino acid level for the SEQ ID NO: 5 (DDIMM) and SEQ ID NO: 6 (KEIMM).

[- - -: Represents gaps, identical sequences are shaded black and similar sequences are shaded grey].

FIG. 8:

Immunodominant 39 amino acid repeat unit with intra repeat variation for the strain MHOM/IN/DD8 of Indian isolate of *L. donovani*, as shown in SEQ ID NO: 5. The first 39 amino acid repeat unit is presented and the degeneracies of various amino acid positions between repeats are indicated

FIG. 9:

Immunodominant 39 amino acid repeat unit with intra repeat variation for the strain MHOM/IN/KE16/1998 of Indian isolate of *L. donovani*, as shown in SEQ ID NO: 6. The first 39 amino acid repeat unit is presented and the degeneracies of various amino acid positions between repeats are indicated.

FIG. 10:

a) The Ni-NTA agarose purified 6x-His tagged recombinant proteins resolved on 12% SDS-PAGE and stained with Coomassie brilliant blue. Lane 1: Pre stained Molecular weight marker (MBI Fermentas, USA), Lane 2: Purified protein from MHOM/IN/DD8 (~29 kDA) lane 3: Purified protein from MHOM/IN/KE16/1998 (~26 kDa).

b) Western blot with Penta anti-His-HRP conjugate for the purified protein. Lane 1: Pre stained Molecular weight marker (MBI Fermentas, USA), Lane 2: Purified protein from MHOM/IN/DD8 (~29 kDA) lane 3: Purified protein from MHOM/IN/KE16/1998(~26 kDa).

[The purified protein from MHOM/IN/KE16/1998 of predicted molecular weight of ~26 kDa has aberrant mobility on SDS-PAGE and was migrating at higher molecular weight ~32 kDa.]

FIG. 11:

a) The Ni-NTA agarose purified 6x-His tagged recombinant proteins resolved on 12% SDS-PAGE and stained with Coomassie brilliant blue. Lane 1: Pre stained Molecular weight marker (MBI Fermentas, USA), Lane 2: Purified protein from MHOM/IN/DD8 (~29 kDA) lane 3: Purified protein from MHOM/IN/KE16/1998 (~26 kDa).

b) Western blot with KA patient sera for the purified protein. Lane 1: Pre stained Molecular weight marker (MBI Fermentas, USA), Lane 2: Purified protein from MHOM/IN/DD8 (~29 kDA) lane 3: Purified protein from MHOM/IN/KE16/1998(~26 kDa).

FIG. 12:

a) The NI-NTA agarose purified 6x-His tagged recombinant proteins resolved on 12% SDS-PAGE and stained with Coomassie brilliant blue. Lane 1: Pre stained Molecular weight marker (MBI Fermentas, USA), Lane 2: Purified protein from MHOM/IN/DD8 (~29 kDA) lane 3: Purified protein from MHOM/IN/KE16/1998 (~26 kDa).

b) Western blot with PKDL patient sera for the purified protein. Lane 1: Pre stained Molecular weight marker (MBI Fermentas, USA), Lane 2: Purified protein from MHOM/IN/DD8 (~29 kDA) lane 3: Purified protein from MHOM/IN/KE16/1998(~26 kDa).

FIG. 13:

a) The Ni-NTA agarose purified 6x-His tagged recombinant proteins resolved on 12% SDS-PAGE and stained with Coomassie brilliant blue. Lane 1: Pre stained Molecular weight marker (MBI Fermentas, USA), Lane 2: Purified protein from MHOM/IN/DD8 (~29 kDA) lane 3: Purified protein from MHOM/IN/KE16/1998 (~26 kDa).

b) Western blot with pooled Healthy control patient's sera (N=5) for the purified protein. Lane 1: Pre stained Molecular weight marker (MBI Fermentas, USA), Lane 2: Purified protein from MHOM/IN/DD8 (~29 kDA) lane 3: Purified protein from MHOM/IN/KE16/1998 (~26 kDa).

FIG. 14:

a) The Ni-NTA agarose purified 6x-His tagged recombinant proteins resolved on 12% SDS-PAGE and stained with Coomassie brilliant blue. Lane 1: Pre stained Molecular weight marker (MBI Fermentas, USA), Lane 2: Purified protein from MHOM/IN/DD8 (~29 kDA) lane 3: Purified protein from MHOM/IN/KE16/1998 (~26 kDa).

b) Western blot with only secondary antibody control for the purified protein. Lane 1: Pre stained Molecular weight marker (MBI Fermentas, USA), Lane 2: Purified protein from MHOM/IN/DD8 (~29 kDA) lane 3: Purified protein from MHOM/IN/KE16/1998(~26 kDa).

FIG. 15:

The graph shows titer value for different groups of sera on ELISA with purified polypeptide (SEQ ID NO:5) of MHOM/IN/DD8 origin. The mean OD value with standard deviation is shown and also depicted in the graph. The different groups included are as follows:

1) Endemic healthy control samples from clinically and serologically (for rK39) negative individuals from an endemic area in Bihar, India, 2). Samples from confirmed VL and PKDL cases (diseased cases) from an endemic area in Bihar, India, 3). Samples from patients positive for HCV, 4) Samples from patients positive for HIV 5). Samples from patients positive for TB, 6) Samples from patients positive for HBs Ag, 7). Non-endemic healthy control samples were obtained from individuals from a non-endemic area (Delhi) for VL.

FIG. 16:

The graph shows titer value for different groups of sera on ELISA with purified polypeptide (SEQ ID NO: 6) of MHOM/IN/KE16/1998 origin. The mean OD value with standard deviation is shown and also depicted in the graph. The different groups included are as follows:

1) Endemic healthy control samples from clinically and serologically (for rK39) negative individuals from an endemic area in Bihar, India, 2). Samples from confirmed VL and PKDL cases (diseased cases) from an endemic area in Bihar, India, 3). Samples from patients positive for TB, 4) Samples from patients positive for HCV 5). Samples from patients positive for HIV, 6) Samples from patients positive for HBs Ag, 7). Healthy control samples are from individuals from a non-endemic area (Delhi) for VL.

BRIEF DESCRIPTION OF THE SEQUENCES IN THE SEQUENCE LISTING

SEQ ID NO: 1 is the nucleotide sequence of full length kinesin related antigen gene from Indian isolate of *L. donovani* strain MHOM/IN/DD8.

SEQ ID NO: 2 is the nucleotide sequence of fall length kinesin related antigen gene from Indian isolate of *L. donovani* strain MHOM/IN/KE16/1998.

SEQ ID NO: 3 is the nucleotide sequence encoding immunodominant 39 amino acid repeat polypeptide from Indian isolate of *L. donovani* strain MHOM/IN/DD8

SEQ ID NO: 4 is the nucleotide sequence encoding immunodominant 39 amino acid repeat polypeptide from Indian isolate of *L. donovani* strain MHOM/IN/KE16/1998.

SEQ ID NO: 5 is the amino acid sequence of a 39 amino acid repeat regionantigen from Indian isolate of *L. donovani* strain MHOM/IN/DD8

SEQ ID NO: 6 is the amino acid sequence of a 39 amino acid repeat regionantigen from Indian isolate of *L. donovani* strain MHOM/IN/KE16/1998

SEQ ID NO: 7 is the synthetic oligonucleotide, LKF 93

SEQ ID NO: 8 is the synthetic oligonucleotide, LKR1803

SEQ ID NO: 9 is the synthetic oligonucleotide, LKF 1527

SEQ ID NO: 10 is the synthetic oligonucleotide, LKF 2564

SEQ ID NO: 11 is the synthetic oligonucleotide, LKR 3266

DETAILED DESCRIPTION OF THE INVENTION

The present invention provides a recombinant antigen developed from the Indian isolates of *L. donovani*, which is a variant of existing recombinant kinesin related antigen (rK39) for diagnosing VL in India and other geographical areas where *L. donovani* is the causative agent. This recombinant antigen of Indian origin varies upto 60% in the predicted amino acid sequence at the immunodominant repeat epitope to that of the rK39. Recently, the kinesin related antigen gene has been cloned and characterized from *L. chagasi* an, American visceralising species by Burns et al.; this led to the development of rK39 antigen, a recombinant protein with 39 amino acid tandem repeats. This above [Burns et al., 1993] antigen from a new world visceralising species *L. chagasi* is reported not sensitive in some highly endemic regions for VL, Sudan and Southern Europe [Zijlstra, E. E., 2001; Jelinek T., 1999] as it is on some other geographical areas, India, Bangladesh, Nepal etc. India carries the majority of the VL population in the global leishmaniasis burden. So, it is very important to have precise and well characterized tools for the diagnosis and other control measurements in India. The applicants have characterized the kinesin related antigen from two strains namely, a) MHOM/IN/DD8 a WHO reference strain originally obtained from a kala-azar patients from Bihar, India and b) MHOM/IN/KE16/1998 obtained from a 10 year old female kala-azar patient from Musafarpur, Bihar, India of *L. donovani* at the sequence level to study, whether the sequence is similar to that one of *L. chagasi* and to rule out the suspicion that, are some cases are going unnoticed in India as in Sudan? Also it becomes very important to know that, are the various ethnic groups responding differently to the rK39 antigen or it is the sequence divergence at the immunodominant region that causes the difference in sensitivity. In this invention we found that, the sequence of kinesin antigen/polypeptide significantly differs from that of the published *L. chagasi* from which the rK39 was derived.

In the present invention we have also raised antibodies against the kinesin antigen/polypeptide and utilized it for the detection of Leishmanial antigens.

Parasites were initially isolated as Promastigotes in NNN medium from clinical samples of Kala-azar patients and subsequently adapted to grow at 25° C. in Medium 199 containing 10% heat inactivated FCS. For routine maintenance, samples of the inoculum containing parasites were introduced aseptically into culture tubes with 4 ml of medium 199 supplemented with 10% FCS. The tubes were placed in cooled incubator at 25° C. and the growth was monitored at regular intervals by microscopy. For mass cultivation of the parasite, samples of inoculum containing parasites were introduced aseptically into 200 ml of M199 containing 10% FCS in a 500 ml tissue culture flask and incubated in a cooled incubator at 25° C. until mid log phase (7-10 days). The parasites were then harvested and used for nuclear DNA isolation.

The parasites in their mid log phase was harvested by centrifuging at 5000 rpm in a refrigerated centrifuge. Parasite nuclear DNA was isolated following standard protocol with minor modifications [Lu H. G. et al., 1994]. Approximately $1\text{-}5\times10^9$ promastigotes were lysed in 10 volumes of lysis buffer (NaCl, 100 mM, Tris-HCl, 10 mM (pH 8.0), EDTA 10 mM, Proteinase K/ml 100 µg, Sarcosyl 1.5%) at 60° C. for 3 hours. The kinetoplast DNA networks were sedimented by centrifugation at 27,000×g for 1 hour and resuspended in TE buffer (Tris-HCl (pH 8.0) 10 mM, EDTA (pH 8.0) 1 mM). The nuclear DNAs were isolated from the supernatants left after sedimentation of the kDNAs. These supernatants were incubated overnight for further digestion of proteins at 65° C. The nuclear DNA was subjected to several cycles of phenol/chloroform extractions by adding equal volume of phenol/chloroform mixture, mixing thoroughly followed by sedimentation by centrifugation at 5000 rpm for 15 minutes. The nuclear DNA was precipitated by adding $\frac{1}{10}^{th}$ the volume of 3M-sodium acetate and 2 volumes of 100% ethanol mixed well and incubated at −20° C. for 1 hour. The mixture was sedimented by centrifugation at 5000 rpm for 30 minutes at 4° C. The pellet was washed with 70% ethanol, dried and resuspended in TE buffer. The concentration and purity of the DNA was measured by taking OD at 260/280 nm. The DNA was stored at −70° C. until use.

The PCR for the amplification of kinesin related antigen was performed as below using 50 ng of the isolated nuclear DNA and using the following primers in various combinations to amplify the overlapping parts in the kinesin gene. The primes were designed based on the sequence data from the GenBank for the kinesin gene (Accession No. L07879). The available kinesin gene sequence from *L. chagasi* is 3319 bp in length and has an ORF from position 454 with a putative ATG starting codon and extends until the last base at position 3319. This gene has 5' non repeat region from the starting codon at position 2563 and a conserved immunodominant repeat domain from base 2564 to till the end in the 3'. The repetitive epitope of 39 amino acid is part of the kinesin gene at the 3' end from the base position 2564 to 3319. This repetitive epitope has 117 bp tandem repeat at 6.5 copies reported and extending upto 3 to 4 kb in the 3' end. The highly conserved short stretches of sequences at various positions were considered for primer designing. The whole 3.33 kb gene of the *L. chagasi* was considered and we attempted to amplify the open reading frame (ORF) from the position 454 to 3319 bp. The main focus being on the immunodominant tandem repeats of 117 bp size; however we attempted to amplify and characterize complete ORF with as many repeats as possible. Three forward and two reverse primers were designed to amplify this gene detailed as follows; the primer LKF93 (SEQ ID NO: 7) is upstream to the predicted starting codon at 455 bp and it covered 362 bp 5' to the starting of ORF. The primer LKF1527 (SEQ ID NO:9) is another forward primer, which starts from the position at the base 1527 from the base one i.e. it covers 1073 bases from the beginning of the ORF. The third forward primer is LKF 2564 (SEQ ID NO: 10) that is intended to amplify the immunodominant tandem repeats in combination with the reverse primer LKR3266 (SEQ ID NO: 11). The first reverse primer is LKR 1803 (SEQ ID NO: 8), which includes an overlapping region of 276 bp with that of the second primer set with another reverse primer LKR3266 (SEQ ID NO: 11). The primer sequences are given in the SEQ ID NO: 7 to SEQ ID NO: 11. The first PCR primer set LKF 93 (SEQ ID NO:7) and LKR 1803 (SEQ ID NO:8) amplified a 1.71 kb fragment from the position at 93 base at the 5' end of the kinesin gene to the position 1803 bp in the 3' position. The second PCR primer set LKF 1527 (SEQ ID NO: 9) and LKR 3266 (SEQ ID NO: 11) amplified a 1.15 kb fragment with one 117 bp tandem repeat. This PCR amplicons had 276 bp overlapping nucleotides at the 5' end with that of first PCR product amplified. The third PCR primer set LKF 2564 (SEQ ID NO: 10) and LKR3266 (SEQ ID NO: 11) amplified the immunodominant 117 tandem repeat region. This third primer set amplified a fragment of size approximately 470 bp corresponding the four 117 bp tandem repeat for MHOM/IN/KE16/1998 and approximately 590 bp size product corresponding five immunodominant tandem repeat for the strain MHOM/IN/DD8. All the PCR products were purified as described below and cloned in pGEMTE cloning vector and sequenced in an automated DNA sequencer.

By using aerosol free pipette tips and keeping the pre- and post-PCR products separately, amplicons carry over contamination was avoided. All PCR reactions were performed using standard protocols (Sambrook et al., 1989) with a set of negative controls.

| | |
|---|---|
| 10× Taq buffer | 5.00 µl |
| 10 mM dNTPs | 1.00 µl |
| Primer Forward (25 µM) | 1.00 µl |
| Primer Reverse (25 µM) | 1.00 µl |

-continued

| | |
|---|---|
| Taq DNA polymerase (5 U/µl) (Promega, USA) | 0.25 µl |
| Template DNA | 2.00 µl |
| Sterile water to make up the volume to | 50.00 µl |

The tubes were kept in thermal cycler (MJ Research, USA) and incubated at 95° C. for 5 minutes followed by 35 cycles of amplification.

The amplified PCR products were resolved on agarose gel electrophoresis. The gel was visualized under ultraviolet transilluminator (UVP) and photographed using a Polaroid camera.

The kinesin gene following amplification by PCR was cloned in a TA cloning vector as below. The PCR amplified DNA were resolved on agarose gel and the portion containing the band of interest was excised with a sterile scalpel. The DNA was eluted from the gel using gel elution kit (Qiagen, Germany) following the manufacturer's protocol. Concentration of eluted DNA was measured by absorbance at 260 nm in spectrophotometer.

The gel purified PCR product of interest was ligated directly in pGEMT-Easy vector. In a 1.5 ml micro centrifuge tube the following components were added.

| | |
|---|---|
| pGEM-T Easy | 1.00 µl |
| 10× ligation buffer | 1.00 µl |
| DNA (200 ng) | 5.00 µl |
| T4 DNA Ligase (2 U/µl) | 1.00 µl |
| Water to make the volume upto | 10.00 µl |

After mixing gently, the tubes were incubated at 4° C. overnight and heated for 10 minutes at 70° C. The samples were stored at −20° C. until transformation.

The ligated mixture was then transformed by heat sock treatment. The competent cells were prepared by using calcium chloride method [Sambrook et al., 1989]. A single colony of *E. coli* was inoculated in 5 ml of LB medium and incubated at 37° C. overnight with shaking (200 rpm). Next day fresh stock of 100 ml LB medium was inoculated with 1 ml of the overnight culture and incubated at 37° C. with continuous shaking until the O.D. reached 0.6 at 600 nm. The culture was chilled on ice for 30 minutes and the cells were harvested by centrifugation at 4000 g, 4° C. for 10 min. The cell pellet was resuspended in $\frac{1}{10}^{th}$ volume of ice cold filtered sterile 50 mM $CaCl_2$ and kept on ice for 30 min. The cells were pelleted down and finally resuspended in $\frac{1}{25}^{th}$ volume of ice-cold 50 mM $CaCl_2$ (with 20% V/V of autoclaved glycerol) and either stored at −70° C. in aliquots of 200 µl or used immediately for transformation.

Approximately 5 µl of ligation mixture was gently mixed with competent cell (200 µl) and incubated in ice for 30 min. After incubation the cells were placed in water bath set at 42° C. for 90 seconds (heat shock) and immediately transferred to ice. 800 µl of LB medium was added to the cells and kept at 37° C. for 90 minutes with shaking (150 rpm). The cells were plated with 16 µl of X-gal and 10 µl of 1M IPTG on LB agar plates containing 50 µg/ml of ampicillin. The plates were incubated at 37° C. for 12-16 hours. The white colonies were selected and checked for the insert. For screening, the Plasmid was isolated by rapid boiling method [Holmes and Quigley, 1981]. The colonies were picked up with sterile toothpick and inoculated in 5 ml of fresh medium. The cultures grown overnight were pelleted and the cells were resuspended in 500

μl of STET buffer (Sucrose 8% (w/v), Tris-HCl, (pH 8.0), 50 mM, EDTA Na₂, (pH 8.0) 50 mM, Triton-X 100 5% (w/v) followed by lysis with 40 μl of lysozyme. The mixture was vortexed well and incubated in a boiling water bath for 90 seconds. The bacterial debris and chromosomal DNA were removed by centrifugation at 12000 g for 10 minutes. The supernatant was mixed with 400 μl of isopropanol and 200 μl of 7.5 M ammonium acetate. The Plasmid DNA was pelleted by centrifugation. The dried pellet was resuspended in 100 μl of sterile water, mixed with 50 μl of 7.5 M ammonium acetate and incubated on ice for 30 minutes. The samples were centrifuged at 4° C. for 10 minutes and Plasmid DNA was precipitated with ethanol. The pure DNA pellet obtained after centrifugation was washed twice with 70% ethanol dried and dissolved in 50 μl of sterile water.

The restriction analysis of the recombinant Plasmid was done using appropriate restriction enzyme sites flanking the multiple cloning site of the vectors. The reaction was set as follows:

| Plasmid DNA | 8.00 μl (2 μg) |
|---|---|
| 10× reaction buffer | 2.00 μl |
| RNase A (10 mg/ml) | 5.00 μl |
| Restriction Enzyme | 5 Units |
| Sterile water to make the volume up to | 20.00 μl |

The reaction was incubated at 37° C. for 6-8 hours and the products were analyzed on 1.5% agarose gel along with standard molecular weight markers. The positive clones containing the insert as detected by the restriction digestion were used for sequencing and preserved as glycerol stock.

All the sequencing was done by chain termination method [Sanger et al., 1977] in an automated DNA sequencer, ABI Prism version 7.0. The Sequences were analyzed using various software like DNASIS, Lasergene: edit; Megalign etc (DNA star Inc.), Clustal W (multiple alignment of various sequence files). All the sequences obtained were aligned to form continuous stretch by using Seqman II (Lasergene package). Along with this, the sequence was searched for homology by using BLAST [Altschul et al., 1997] option from various websites.

Figure 2:
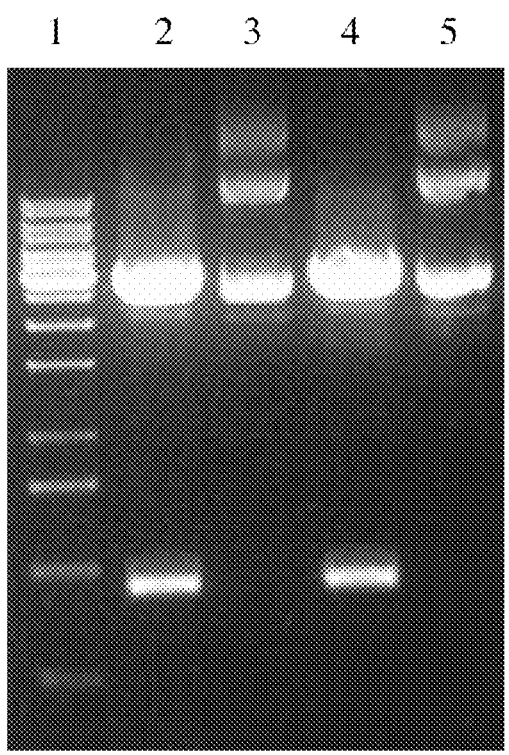

The fall-length kinesin sequence obtained after assembling the sequence was presented in the SEQ ID NO: 1 for the strain MHOM/IN/DD8, it was found to be 3016 bp in length with an open reading frame of 2670 bp. The length of the sequence for the strain MHOM/IN/KE16/1998 was found to be 2937 bp with a long open reading frame of 2577 bp (SEQ ID NO: 2). The sequence analysis revealed that the size of the PCR product amplifying the immunodominant region was 563 bp for the strain MHOM/IN/DD8 (FIG. 1) corresponding to 4.8 tandem repeats of 117 bp corresponding to 4.8 units of 39 amino acid repeats and 466 bp for the strain MHOM/IN/KE16/1998 (FIG. 2) corresponding to 4 tandem repeats of 117 bp (4 units of 39 amino acid repeats).

Further, the sequence analysis shows significant variation in both at DNA level as well as in the predicted amino acid sequence from that of the L. chagasi sequence. The strain MHOM/IN/DD8 shows enormous variation from that of L. chagasi as well as from the strain MHOM/IN/KE16/1998. The blast search for predicted protein sequence of the strain MHOM/IN/DD8 (SEQ ID NO:5) using non-redundant and patent division of GenBank database reveals only up to 38% identity with that of published L. chagasi and US patent nos. i) U.S. Pat. No. 5,411,865 and ii) U.S. Pat. No. 5,912,166 respectively FIG. 3.

The clustal W multiple sequence alignment of the immunodominant repeat region at the nucleotide level for the L. donovani strains MHOM/IN/DD8 and MHOM/IN/KE16/1998 (SEQ ID NO: 3 and SEQ ID NO: 4) with that of the immunodominant repeat region of L. chagasi was done and presented in the FIG. 4. The identities are shadowed dark. The multiple sequence alignment of the immunodominant repeat region at the amino acid level between L. donovani (SEQ ID NO: 5 and SEQ ID NO: 6) L. chagasi is presented in FIG. 5. Multiple sequence alignment of the immunodominant repeat region at the amino acid level for the L. donovani strain MHOM/IN/DD8 (SEQ ID NO:5) with that of the immunodominant repeat region of L. chagasi is presented in the FIG. 6. Sequence alignments of the immunodominant repeat region at the amino acid level for the two L. donovani strains MHOM/IN/DD8 and MHOM/IN/KE16/1998 (SEQ ID NO: 5 and SEQ ID NO: 6) is presented in FIG. 7. Immunodominant 39 amino acid repeats unit with intra repeat variation for the Indian isolates of L. donovani, strains MHOM/IN/DD8 and MHOM/IN/KE16/1998 (SEQ ID NO: 5 and SEQ ID NO: 6) are presented in FIG. 8 and FIG. 9. The sequence analysis reveals that, the amino acids varies enormously having many substitution both conserved and variable at many positions in the 39 amino acid sequence reported for L. chagasi. At least five amino acids for L. donovani are different to L. chagasi at positions 18, 27, 29, 32 and 38 indicated by "*" in the table 1 below, After analyzing the sequences insilico we found a significant variation in the amino acid sequence at the immunodominant region of the strain MHOM/IN/DD8 with that of the L. chagasi. Then, to confirm whether the sequence variation causes any effect on the performance of the antigen to detect anti leishmanial antibodies, we expressed the immunodominant region from the two Indian Leishmania donovani isolates in E. coli expression vector pRSET (Invitrogen) as 6×-His tagged protein. We have expressed various combinations of the immunodominant repeat like one, two, three, four, 4.8 units and one repeat with the 889 nucleotides upstream to the immunodominant domain. We found that recombinant peptides with four and 4.8 repeat units having higher sensitivity and specificity. Thus, our work was focused on polypeptides containing 4.0 and 4.8 repeat units of 39 amino acids.

The E. coli expression vector pRSET C (Invitrogen, Netherlands) was completely digested with PstI and NcoI restriction enzymes at 37° C. overnight. The digested plasmid was fractionated on agarose gel to remove the stuffer fragment. The plasmid band was excised and eluted by Qiagen gel elution system and stored in −20° C. until further use.

The insert was released from the recombinant pGEM-TE plasmid carrying the immunodominant tandem repeats (pGEM-TEasy/DD8/LKF2564 and pGEM-TEasy/KE16/LKF2564) by digesting it with PstI and NcoI. The inserts was excised from the gel, eluted by Qiagen gel elution system and ligated in PstI and NcoI digested pRSET C vector in-frame and transformed to BL21 competent cells by the standard protocol [Sambrook et al., 1989]. The clones were selected on the ampicillin plates and plasmid DNA was isolated and digested with PstI and NcoI to check for the insert. The clones, which released the insert, were selected for protein induction.

TABLE 1

| Amino Acid Position | MHOM/IN/DD8 (SEQ ID NO: 5) | MHOM/IN/ KE16/1998 (SEQ ID NO: 6) | L. chagasi (Reed USPTO: 5,411,865) |
|---|---|---|---|
| 1 | K, L, A & S | L | L |
| 2 | E | E | E |
| 3 | Q, G, V, A | Q | Q |
| 4 | Q, R | Q, R | Q |
| 5 | L, A | L | L |
| 6 | R, A | R | R |
| 7 | D, E | D, E | D, E |
| 8 | S, L | S | S |
| 9 | E, A | E | E |
| 10 | T, R, G & A | E, A | E, A |
| 11 | R, K, V & Q | R, H | R |
| 12 | A, L | A | A |
| 13 | A, E, K | A | A |
| 14 | E, A & S | E | E |
| 15 | L, T, A | L | L |
| 16 | K, A | M, K & A | A |
| 17 | A, S | R, A & S | S |
| 18* | E, A & V | K, Q | Q |
| 19 | L, K | L | L |
| 20 | E, N, T & S | E | E |
| 21 | A, L, & S | A, S | A, S |
| 22 | T, V & M | T | T |
| 23 | A, E | A | A, T |
| 24 | A, Q | A | A |
| 25 | A, D & E | A | A |
| 26 | K, R | K | K |
| 27* | T, E | S, T | M, S |
| 28 | S, R & N | S | S |
| 29* | V, T | A | A |
| 30 | E, R | E | R |
| 31 | Q, A | Q | Q |
| 32* | E, T & A | D | D |
| 33 | R, L | R | R |
| 34 | E | E | E |
| 35 | K, E & Q | N | N, Q |
| 36 | T, R & Q | T | T |
| 37 | R, L | R | R |
| 38* | T, R | A | A |
| 39 | A, I, E & L | T, A | T, A |

Then, a single recombinant *E. coli* (BL 21) colony containing the insert was inoculated in 2 ml of SOB containing Ampicillin (50 μg/ml) and incubated overnight at 37° C. with shaking (225 rpm). The next day, 25 ml of SOB was inoculated with the overnight culture and allowed to grow at 37° C. with shaking to an $OD_{600}$ of 0.6. Removed 1 ml aliquot of cells, centrifuged and frozen in −20° C. To the culture added IPTG to a final concentration of 1 mM and incubated at 37° C. with shaking. A time course of expression to determine the optimal induction time for maximum expression of protein was done by taking aliquot of cells at 1, 2, 3, 4 & 5 hours after induction with IPTG and analyzed by SDS-PAGE and western blot. Further, to determine the protein solubility, a single recombinant *E. coli* (BL 21) colony containing the insert was inoculated in 2 ml of SOB containing Ampicillin (50 μg/ml) and incubated overnight at 37° C. with shaking (225 rpm). The next day, 25 ml of SOB was inoculated with the overnight culture and allowed to grow at 37° C. with shaking to an $OD_{600}$ of 0.6. Removed 1 ml aliquot of cells, centrifuged and frozen in −20° C. To the culture added IPTG to a final concentration of 1 mM and incubated at 37° C. with shaking for additional 4 hours. The cells were harvested by centrifugation at 4000×g for 20 minutes and the pellet was resuspended lysis buffer for purification under native conditions (Qiagen, Germany) and lysed by sonication, 6×10 s with 10 s pauses at 200-300 W. The lysate was centrifuged in a refrigerated centrifuge for 10 minutes at 10,000×g. The supernatant was transferred to a fresh tube and the pellet was resuspended in lysis buffer and preserved on ice. The pellet and the supernatant was mixed with 2×SDS-PAGE sample buffers separately and analyzed by using 12% SDS-PAGE and western blot. The results show that the protein is detectable in the soluble fraction and thus can be purified under native conditions.

The maximum protein-producing clones were inoculated in 20 ml of SOB containing 100 μg/ml Ampicillin and grew overnight at 37° C. with vigorous shaking. The next day, 1 liter of SOB was inoculated with 1:50 noninduced overnight culture and allowed to grow at 37° C. with shaking until an $OD_{600}$ of 0.6 is reached. A 5 ml aliquot of culture was taken immediately before induction. The cells were induced by adding IPTG to a final concentration of 1 mM and continued incubation at 37° C. for 4 hours. The cells were harvested by centrifugation at 4000×g for 20 minutes and stored in −20° C. until purification.

The recombinant protein was purified using Ni-NTA agarose column (Qiagen, Germany) tinder native conditions following the manufacturer's protocol. The cell pellets were thawed for 15 minutes on ice and resuspended in lysis buffer at 5 ml per gram wet weight. To this lysozyme was added at 1 mg/ml and incubated for 30 minutes on ice and sonicated on ice using six 10 s bursts at 200-300 W with a 10 s cooling period between each burst. The lysate was centrifuged at 10,000×g for 30 minutes at 4° C. to sediment the cellular debris. The supernatant was saved. All aliquot of 50 μl supernatant was taken and stored in −20° C. for analysis later. Added 1 ml of the 50% Ni-NTA slurry to 4 ml of cleared lysate and mixed gently by shaking (200 rpm on a rotary shaker) at 4° C. for 60 minutes. The lysate-Ni-NTA mixture was loaded on to a column with the bottom outlet capped. The flow-throw was collected after removing the bottom cap and the column was washed twice with 4 ml of wash buffer and the fractions were collected for SDS-PAGE analysis. The protein was eluted 4 times with 0.5 mm of elution buffer and the eluate was collected in 4 tubes and analyzed by SDS-PAGE. The protein expression after purification was found to be 4 mg/liter.

For analysis of the expressed protein, Mini gel electrophoresis unit (Bangalore Genei, India) was used. The SDS-PAGE was carried out as per defined protocols [Laemmeli, 1970]. A 10% resolving gel was prepared by mixing the following components: 2.66 ml water, 1.562 ml 30% acrylamide, 1.250 ml 1.5M Tris-HCl, 50 μl 10% APS, 10% TEMED. The gel top was with ~400 μl of water saturated butanol and allowed to polymerize. After polymerization, butanol was drained off and washed with distilled water. Then, 2 ml of stacking gel mix (1.25 ml water, 250 μl 30% acrylamide, 500 μl 0.5M Tris-HCl, 30 μl 10% APS and 5 μl TEMED) was poured carefully avoiding any air bubble on the top of the resolving gel. The comb was inserted in the stacking gel portion and left for polymerization. Following the polymerization the wells were washed with excess amount of water. The samples were applied to the defined wells in the stacking gel and electrophoresis carried out at a constant voltage (60V for stacking and 100V for resolving gel). Standard molecular protein markers (MBI) and control (vector protein) were run alongside the samples. The completed gel was then stained in Coomassie brilliant blue stain, destained and visualized against white light.

The purified protein from the strain MHOM/IN/DD8 migrated at a size of 29 kDa in correlation to the predicted molecular weight and the predicted molecular weight for the strain MHOM/IN/KE16/1998 was 26 kDa but the purified protein from this strain had aberrant PAGE mobility and was migrating at higher molecular weight ~32 kDa (FIG. 10a). The reported antigens are entirely different from the *Leish-*

*mania chagasi* 230 kDa antigen. The antigen varies significantly, more than 60% in its predicted amino acid sequence to that of K39 repeat antigen from *L. chagasi*. Also disclosed are DNA encoding the 29 kD and 26 kD antigen and therapeutic and vaccine compositions comprising the antigens.

Purified recombinant polypeptides from the strains MHOM/IN/DD8 and MHOM/IN/KE16/1998 was used for immunization in rabbits. 100 micro gram of each polypeptide was emulsified with equal volume of Freund's complete adjuvant (Sigma, USA). The mixture was injected intradermally at multiple sites. Three booster doses of the same amount of antigen emulsified with incomplete Freund's adjuvant were given at 30-day intervals. Prior to the first immunization, preimmune serum was collected and tested on western blots. Blood was collected aseptically from the immunized animals 12 days after the last booster, sera was separated and stored on −70° C. until use.

The *E. coli* expressed protein was resolved on to 12% SDS-PAGE followed by electro transfer to nitrocellulose membrane [Towbin et al., 1976]. The transfer was carried out using transfer buffer (Tris base 3.08 g, Glycine 14.66 g, Methanol 200 ml, Water to the final volume of 1000 ml) in Bio-Rad semi dry transfer unit. For transfer, 15V was applied and allowed to run for 45 minutes at room temperature. After transfer the membrane was put in a blocking solution containing 2.5% BSA in phosphate buffered saline (PBS, NaCl 8.00 g, KCl 0.20 g, $NaH_2PO_4$ 1.44 g, $KH_2PO_4$ 0.24 g, pH 7.4). The blocked membrane was washed three times with PBS containing 0.02% Tween-20 (PBS-T). The membrane was incubated with kala-azar patient serum (1:200 diluted in PBS) for 1 hour at 25° C. Further it was washed 4 times in PBS-T and incubated in 1:4000 diluted anti-human IgG antibodies, conjugated with alkaline phosphatase for 45 minutes at room temperature. After several washes with PBS, the membrane was developed by addition of BCIP-NBT (Amresco, USA).

The purified antigens were first run on SDS-PAGE and the subjected to immunoblot with penta-anti-his HRP conjugate antibody (FIGS. 10*a* and 10*b*). To study the antigenicity of the purified proteins, SDS-PAGE followed by immunoblot was carried out with kala-azar patient's sera (FIGS. 11*a* and 11*b*) and immunoblot with PKDL patient's sera (FIGS. 12*a* and 12*b*) followed by western with pooled (n=5) healthy individuals sera as control was done and presented in FIGS. 13*a* and 13*b*. Also, immunoblot with only AP-labelled anti-human secondary antibody was done as shown in FIGS. 14*a* and 14*b*. The results of the immunoblot and sequence analysis reveal that, the recombinant antigens from *L. donovani* are specific in spite of having different epitope.

After protein estimation by BCA method (Sigma, the purified antigen was taken for evaluation by ELISA. The ELISA was standardized initially at different parameters with appropriate serum and reagent controls. The ELISA at 50 ng/well and 1:100 dilutions of sera was chosen optimal and used the same conditions for ELISA with two antigens from *L. donovani* viz. MHOM/IN/DD8 and MHOM/IN/KE16/1998. In each plate one positive control (parasitologically and serologically positive for rK39) and one negative control with sera from non-endemic region another with reagent control was included. The plates were coated as below; Polystyrene micro titer plates with 96 flat-bottom wells were coated with antigen following standard protocol with minor modifications [Singh S et al., 1995] by adding 50 ng of purified kinesin antigen in 200 μl of 0.1M bicarbonate buffer, pH 9.2. The plates were covered and incubated overnight at 4° C. The antigen solution was then removed and plates were washed 3 times in PBST (PBS with 0.05% Tween 20). The wells were then blocked with 200 μl of 1% BSA for 1 hour, washed 3 times with PBST. The plates were dried at room temperature, sealed, and stored at 4° C. until use. The sensitized plates were incubated for 2 hours with 50 μl of patient serum diluted from 1:100 to the end point in PBST. The wells were washed again with PBST and incubated with 50 μl of goat anti-human IgG conjugated with alkaline phosphatase at $10^{-3}$ dilution for another 2 hour, followed by washing 3 times with PBST. After incubation for 30 minutes at 37° C. with 50 μl of p-nitrophenylphosphate in diethylamine buffer, the reaction was stopped with 50 μl of 3N NaOH. The optical density of each well was measured at 450 nm in a Tritrius plate reader. The antibody titers to the recombinant protein from MHOM/IN/DD8 (SEQ ID NO:5) were considerably lower to that of MHOM/IN/KE16/1998 (SEQ ID NO: 6) for the same group of samples. The preliminary studies with 72 Endemic and 80 non-endemic healthy controls, 92 Tuberculosis positive, 32 HIV positive, 31 HCV positive and 27 HbsAg positive sera showed no cross reactivity. However, the rK39 positive previously confirmed cases of 10 VL and 10 PKDL sera show high antibody titer with both the antigens at 50 ng/well concentration. The data show that, these two well-characterized antigens from the Indian strains will be highly useful for the Kala-azar diagnosis in India.

The FIG. 15 depicts the mean titer value of different samples subjected to ELISA using purified antigen of MHOM/IN/DD8 origin and the FIG. 16 show the mean titer value of different set of samples for the purified antigen of MHOM/IN/KE16/1998 origin.

*Leishmania* Antigen Detection Using Antibody

Purified recombinant polypeptides from the strains SEQ ID NO: 5 and SEQ ID NO: 6 were used for immunization in rabbits. 100 micro gram of each polypeptide was emulsified with equal volume of Freund's complete adjuvant (Sigma, USA). The mixture was injected intradermally at multiple sites. Three booster doses of the same amount of antigen emulsified with incomplete Freund's adjuvant were given at 30-day intervals. Prior to the first immunization, preimmune serum was collected and tested on western blots. Blood was collected aseptically from the immunized animals 12 days after the last booster, sera were separated and the antibody present in the sera was affinity purified and stored at 4° C. until use.

Polystyrene micro titer plates with 96 wells were coated by diluting the antibody stored at 4° C. in coating buffer (pH 9.2) [1.59 g sodium carbonate ($Na_2CO_3$), 2.93 g sodium bicarbonate ($NaHCO_3$), 0.20 g sodium azide ($NaN_3$), dissolved in 900 ml $H_2O$, adjusted pH to 9.6 with HCl and make up to 1 L] and added 200 μl to each well of a microtitre plate. The plates were incubated at 37° C. for 4 h and washed with PBS-Tween, three times. The plates dried by tapping upside down on tissue paper. The antibody coated to the solid support then was used for the detection of *Leishmania* antigen this method called a double antibody or sandwich ELISA, and was performed as below. To each well added 200 μl aliquots of the test sample and incubated for 4-hours at 37° C. the plates are washed three times with PBST and then incubated with antibody conjugate and incubated at 37° C. for 2 hours washed three times with PBST and added 200 μl aliquots of substrate to each well and incubated at room temperature for 60 min. The optical density of each well was measured at 405 nm in a Tritrius® plate reader. The sandwich ELISA measures the amount of antigen between two layers of antibodies. The *leishmania* antigen to be measured contains at least two antigenic sites, capable of binding to antibody, since at least two antibodies act in the sandwich. So sandwich assays are restricted to the quantitation of multivalent antigens such as proteins or polysaccharides. Sandwich ELISA for quantitation of antigens are especially valuable when the concentration of antigens is low and/or they are contained in high concentrations of contaminating protein The following examples illustrate the invention, which should not be construed to limit the scope of the invention.

Example 1

This example illustrates the cloning of kinesin immunodominant repeat region from Indian isolates of *L. donovani*. A PCR cloning strategy was followed using a primer set LKF 2564 and LKR 3266 (SEQ ID NO: 10 and SEQ ID NO: 11 respectively) to amplify the immunodominant 117 tandem repeat region. This primer set amplified a fragment of size approximately 470 bp corresponding to the four 117 bp tandem repeat from *L. donovani* strain MHOM/IN/KE16/1998 and approximately 590 bp size product corresponding five immunodominant tandem repeat from *L. donovani* strain MHOM/IN/DD8. The kinesin gene following amplification by PCR was cloned in a TA cloning vector as below. The PCR amplified DNA were resolved on agarose gel and the portion containing the band of interest was excised with a sterile scalpel. The DNA was eluted from the gel using gel elution kit (Qiagen, Germany) following the manufacturer's protocol. Concentration of eluted DNA was measured by absorbance at 260 nm in spectrophotometer.

The gel purified PCR product of interest was ligated directly in pGEMT-Easy vector (Promega, USA). In a 1.5 ml micro centrifuge tube the following components were added.

| | |
|---|---|
| pGEM-T Easy (100 ng/μl) | 1.00 μl |
| 10× ligation buffer | 1.00 μl |
| DNA (200 ng) | 5.00 μl |
| T4 DNA Ligase (2 U/μl) | 1.00 μl |
| Water to make the volume upto | 10.00 μl |

After mixing gently, the tubes were incubated at 4° C. overnight and heated for 10 minutes at 70° C. The samples were stored at −20° C. until transformation. The ligated mixture was then transformed by heat sock treatment. The competent cells were prepared by using calcium chloride method [Sambrook et al., 1989]. A single colony of *E. coli* was inoculated in 5 ml of LB medium and incubated at 37° C. overnight with shaking (200 rpm). Next day fresh stock of 100 ml LB medium was inoculated with 1 ml of the overnight culture and incubated at 37° C. with continuous shaking until the O.D. reached 0.6 at 600 nm. The culture was chilled on ice for 30 minutes and the cells were harvested by centrifugation at 4000 g, 4° C. for 10 min. The cell pellet was resuspended in $1/10^{th}$ volume of ice cold filtered sterile 50 mM $CaCl_2$ and kept on ice for 30 min. The cells were pelleted down and finally resuspended in $1/25^{th}$ volume of ice-cold 50 mM $CaCl_2$ (with 20% V/V of autoclaved glycerol) and either stored at −70° C. in aliquots of 200 μl or used immediately for transformation.

Approximately 5 μl of ligation mixture was gently mixed with competent cell (200 μl) and incubated in ice for 30 min. After incubation the cells were placed in water bath set at 42° C. for 90 seconds (heat shock) and immediately transferred to ice. 800 μl of LB medium was added to the cells and kept at 37° C. for 90 minutes with shaking (150 rpm). The cells were plated with 16 μl of X-gal and 10 μl of 1M IPTG on LB agar plates containing 50 μg/ml of ampicillin. The plates were incubated at 37° C. for 12-16 hours. The white colonies were selected and checked for the insert. The recombinant clones were further characterized by restriction mapping and sequencing. All the sequencing was done by chain termination method [Sanger et al., 1977] in an automated DNA sequencer, ABI Prism version 7.0. The Sequences were analyzed using various software like DNASIS, Lasergene: edit; Megalign etc (DNA star Inc.), Clustal W (multiple alignment of various sequence files). All the sequences obtained were aligned to form continuous stretch by using Seqman II (Lasergene package).

Along with this, the sequence was searched for homology by using BLAST [Altschul et al., 1997] option from various websites.

The full-length kinesin sequence obtained after assembling the sequence was presented in the SEQ ID NO: 1 for the strain MHOM/IN/DD8, it was found to be 3016 bp in length with an open reading frame of 2670 bp. The length of the sequence for the strain MHOM/IN/KE16/1998 was found to be 2937 bp with a long open reading frame of 2577 bp (SEQ ID NO: 2). The sequence analysis revealed that the size of the PCR product amplifying the immunodominant region was 563 bp for the strain MHOM/IN/DD8 (FIG. 1) corresponding to 4.8 tandem repeats of 117 bp and 466 bp for the strain MHOM/IN/KE16/1998 (FIG. 2) corresponding to 4 tandem repeats of 117 bp.

Further, the sequence analysis shows significant variation in both at DNA level as well as in the predicted amino acid sequence from that of the reported *L. chagasi* sequence (GenBank, Accession No. L07879). The strain MHOM/IN/DD8 shows significant variation from that of *L. chagasi* as well as from the strain MHOM/IN/KE16/1998. The blast search for predicted protein sequence of the strain MHOM/IN/DD8 (SEQ ID NO:5) using non-redundant and patent division of GenBank database reveals only up to 38% identity with that of published *L. chagasi* and US patent nos. i) U.S. Pat. No. 5,411,865 and ii) U.S. Pat. No. 5,912,166 respectively FIG. 3.

Figure 14:
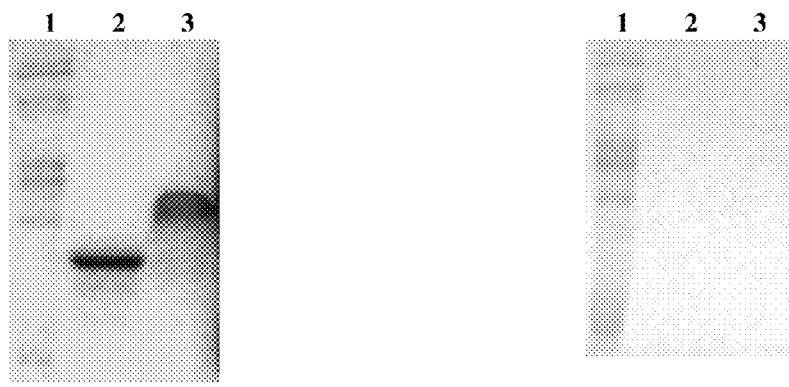

The clustal W multiple sequence alignment of the immunodominant repeat region at the nucleotide level for the *L. donovani* strains MHOM/IN/DD8 and MHOM/IN/KE16/1998 (SEQ ID NO: 3 and SEQ ID NO: 4) with that of the immunodominant repeat region of *L. chagasi* (GenBank, Accession No. L07879) was done and presented in the FIG. 4. The identities are shadowed dark. The multiple sequence alignment of the immunodominant repeat region at the amino acid level between *L. donovani* (SEQ ID NO: 5 and SEQ ID NO: 6) and *L. chagasi* is presented in FIG. 5. Multiple sequence alignment of the immunodominant repeat region at the amino acid level for the *L. donovani* strain MHOM/IN/DD8 (SEQ ID NO:5) with that of the immunodominant repeat region of *L. chagasi* is presented in the FIG. 6. Sequence alignments of the immunodominant repeat region at the amino acid level for the two *L. donovani* strains MHOM/IN/DD8 and MHOM/IN/KE16/1998 (SEQ ID NO: 5 and SEQ ID NO: 6) is presented in FIG. 7. Immunodominant 39 amino acid repeats unit with intra repeat variation for the Indian isolates of *L. Donovani*, strains MHOM/IN/DD8 and MHOM/IN/KE16/1998 (SEQ ID NO: 5 and SEQ ID: 6) are presented in FIG. 8 and FIG. 9. The sequence analysis reveals that, the amino acids vary significantly having many substitutions. These substitutions are conserved or are variable at many positions in the 39 amino acid repeated region reported for *L. chagasi*. At least five amino acids for *L. donovani* are different to *L. chagasi* at positions 18, 27, 29, 32 and 38 indicated by "*" in the table 1.

Example 2

This example illustrates the reactivity of patient sera to recognize the recombinant *L. donovani* antigens. The insert was released from the recombinant pGEM-TE plasmid carrying the immunodominant tandem repeats (pGEM-TEasy/DD8/LKF2564 and pGEM-TEasy/KE16/LKF2564) by digesting it with PstI and NcoI. The inserts was excised from the gel, eluted by Qiagen gel elution system and ligated in PstI and NcoI digested pRSET C vector in-frame and transformed to BL21 competent cells by the standard protocol [Sambrook et al., 1989]. The clones were selected on the ampicillin plates and plasmid DNA was isolated and digested with PstI and NcoI to check for the insert. The clones, which released the insert, were selected for protein expression. The maximum protein-producing clones were inoculated in 20 ml of SOB medium containing 100 µg/ml Ampicillin and grown overnight at 37° C. with vigorous shaking. The next day, 1 liter of SOB medium was inoculated with 1:50 noninduced overnight culture and allowed to grow at 37° C. with shaking until an $OD_{600}$ of 0.6 is reached. A 5 ml aliquot of culture was taken immediately before induction. The cells were induced by adding IPTG to a final concentration of 1 mM and continued incubation at 37° C. for 4 hours. The cells were harvested by centrifugation at 4000×g for 20 minutes and stored in –20° C. until purification. The recombinant polypeptide was purified using Ni-NTA agarose column (Qiagen, Germany) under native conditions following the manufacturer's protocol. The purified protein from the strain MHOM/IN/DD8 migrated at a size of 29 kDa (FIG. 10a, lane 2) that correlates with the predicted molecular weight. The purified antigens were first run on SDS-PAGE (FIGS. 10a, 11a, 12a and 13a) and the subjected to immunoblot with penta-anti-his HRP conjugate antibody (FIG. 10b), kala-azar patient's sera (FIG. 11b), PKDL patient's sera (FIG. 12b) followed by western with pooled (n=5) healthy individuals sera (FIG. 13b), with only AP-labelled anti-human secondary antibody (FIG. 14b) were done. The results of the immunoblot and sequence analysis reveal that, the recombinant antigens from *L. donovani* are specific in spite of having different epitope.

Example 3

This example illustrates the reactivity of patient sera to recognize the *L. donovani* antigens. Protein estimation was done by BCA method (Sigma, USA) and the purified antigens were used for ELISA. The ELISA was standardized initially at different parameters with appropriate serum and reagent controls. The ELISA at 50 ng/well and 1:100 dilutions of sera was chosen optimal and used the same conditions for ELISA with two recombinant polypeptides from *L. donovani* viz. MHOM/IN/DD8 (SEQ ID NO:5) and MHOM/IN/KE16/1998 (SEQ ID NO: 6). In each plate one positive control (parasitologically and serologically positive for rK39) and one negative control with sera from non-endemic region and another with reagent control was included. The plates were coated as below; Polystyrene micro titer plates with 96 flat-bottom wells were coated with antigen following the protocol as reported by Singh S et al., [2002] with minor modifications by adding 50 ng of purified kinesin antigen in 200 µl of 0.1M bicarbonate buffer, pH 9.2. The plates were covered and incubated overnight at 4° C. The antigen solution was then removed and plates were washed 3 times in PBST (PBS with 0.05% Tween-20). The wells were then blocked with 200 µl of 1% BSA for 1 hour, washed 3 times with PBST. The plates were dried at room temperature, sealed, and stored at 4° C. until use. The sensitized plates were incubated for 2 hours with 50 µl of patient serum diluted from 1:100 to the end point in PBST. The wells were washed thrice with PBST and incubated with 50 µl of goat anti-human IgG conjugated with alkaline phosphatase at $10^{-3}$ dilution for another 2 hour, followed by washing 3 times with PBST. After incubation for 30 minutes at 37° C. with 50 µl of p-nitrophenylphosphate in diethylamine buffer, the reaction was stopped with 50 µl of 3N NaOH. The optical density of each well was measured at 450 nm in a Tritrius® plate reader. The antibody titers to the recombinant protein from MHOM/IN/DD8 (SEQ ID NO:5) were considerably lower to that of MHOM/IN/KE16/1998 (SEQ ID NO: 6) for the same group of samples. The preliminary study carried out with sera from 72 Endemic and 80 non-endemic healthy controls, 92 Tuberculosis positive, 32 HIV positive, 31 HCV positive and 27 HBsAg positive individuals. These ELISA results showed 100% specificity with no cross reactivity. However, ELISA carried out for confirmed VL (N=10) and PKDL (N=10) patient's sera with rK39 antigen from *L. chagasi* (Burns et al., 1993), *L. donovani* antigen from the strains MHOM/IN/DD8 (SEQ ID NO:5) and MHOM/IN/KE16/1998 (SEQ ID NO: 6) show high antibody titer for all three antigens at 50 ng/well concentration. The data show that, these two well-characterized antigens from the Indian strains are highly specific and sensitive for the kala-azar diagnosis in India. In a study conducted with more samples it was found that considerable number of cases that could not be diagnosed by rK39 of *L. chagasi* was detected by these two recombinant polypeptides from *L. donovani*. This reveals that, the newly isolated recombinant polypeptides from Indian strains of *L. Donovani* are more specific for the diagnosis of VL and PKDL in India thus they can be used for diagnosis of this disease extensively.

Figure 15:
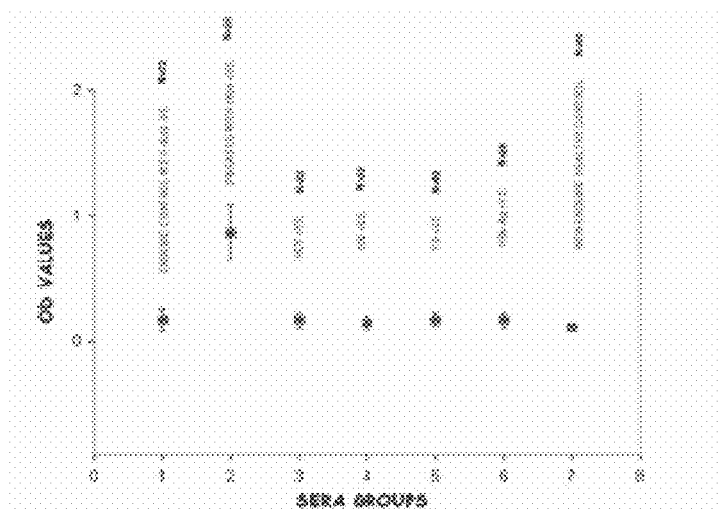
Figure 16:
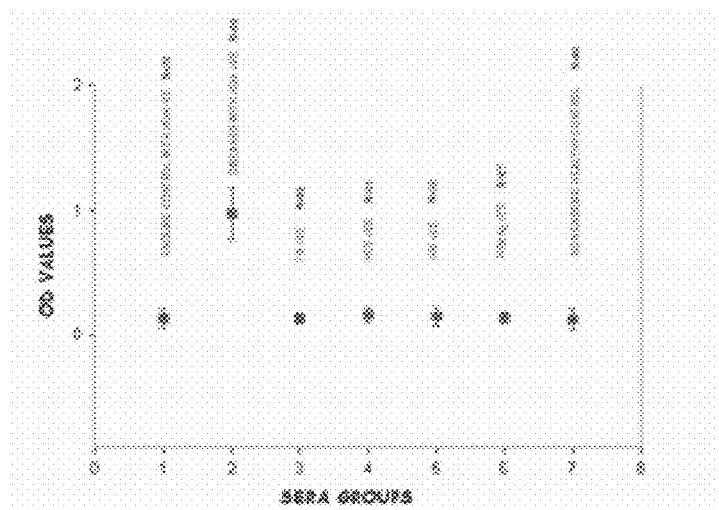

However, only the data pertaining to 10 positive samples and other control samples are presented in FIG. 15 and FIG. 16. The FIG. 15 depicts the mean titer value of different samples subjected to ELISA using purified antigen of MHOM/IN/DD8 origin and the FIG. 16 show the mean titer value of different set of samples for the purified antigen of MHOM/IN/KE16/1998 origin.

Example 4

This example teaches obtaining antibody against the polypeptides SEQ ID NO: 5 or SEQ ID NO; 6 from an animal and its use in the detection of *Leishmania* antibody as below;
1. Purified recombinant polypeptides from the group containing SEQ ID NO: 5 and SEQ ID NO: 6 were used for immunization in rabbits. 100 micro gram of the polypeptide was emulsified with equal volume of Freund's complete adjuvant (Sigma, USA).
2. The mixture was injected intradermally at multiple sites.
3. Three booster doses of the same amount of antigen emulsified with incomplete Freund's adjuvant were given at 30-day intervals. Prior to the first immunization, preimmune serum was collected and tested on western blots.
4. Blood was collected aseptically from the immunized animals 12 days after the last booster, sera were separated and the anti-antibody present in the sera was affinity purified and stored at 4° C. until use.
5. The antibody was first diluted in 0.1M Bicarbonate buffer, pH 9.2 and then 200 µl are added to each well of the microtiter plate.
6. The antibody coated plate was covered with Paraffin and incubated in the cold room overnight in a moist box containing a wet paper towel or at room temperature and humidity for two hours.
7. The plate is emptied and the unoccupied sites are blocked with 100 µl of blocking buffer containing 100 mM phosphate buffer, pH 7.2, 1% BSA, 0.5% Tween-20 and 0.02% Thimerosol for 30 min at room temperature.

8. The plate is emptied and washed three times with wash buffer (100 mM phosphate buffer, 150 mM NaCl, 0.2% BSA and 0.05% Tween 20).
9. The antigen solution is first diluted in antigen buffer (100 mM phosphate buffer, 150 mM NaCl) and then added to the plate in a volume of 50 µl per well. The plate is incubated at room temperature for 45 min to one hour.
10. The plate is emptied again and washed three times with wash buffer.
11. The enzyme-labeled antibody against antigen is diluted appropriately in 0.1M Bicarbonate buffer, pH 9.2 and then 50 µl is added to each well and incubated at room temperature for 30 min.
12. The plate is emptied again and washed three times with wash buffer.
13. The color development system is added and the color intensities are measured.

Advantages

The characterization of the kinesin related antigen at the sequence level has revealed the similarities and differences for the kinesin antigen between two species *L. donovani* and *L. chagasi*.

It is clear from this invention that the immunodominant repeat of kinesin related antigen isolated from Indian strains is different from the earlier reported sequences of other *Leishmania* species.

This study revealed that the Indian strains are quite different from the earlier reported strains and species from other geographical regions.

The study also revealed that amino acid sequence variation between the repeat units of the Indian strains is very high than for previously reported sequences.

This invention has led to the isolation of polypeptide, which is different in sequence from that of earlier reported polypeptide sequence.

This invention has led to the development of a method for detection of antileishmanial antibodies based on the newly found antigens from Indian isolates of *L. donovani*.

This invention has led to the leishmaniasis detection kit for the detection of VL due to species of *L. donovani* of India and other similar species which would have been missed by K39 polypeptide

REFERENCES

1. Altschul, S. F., Madden, T. L., Schaffer, A. A., Zhang, Z., Miller, W. and Lipman, D. 1997. Gapped BLAST and PSI-BLAST: a new generation of protein database search programs, J. Nucleic Acids Res. 25: 3389-3402.
2. Attar Z J, Chance M L, el-Safi S, Carney J, Azazy A, El-Hadi M, Dourado C, Hommel M. 2001. Latex agglutination test for the detection of urinary antigens in visceral leishmaniasis. Acta Trop. 78 (1): 11-6.
3. Badaro, R., D. Benson, M. C. Eulalio, M. Freire, S. Cunha, E. M. Netto, D. Pedral-Sampaio, C. Madureira, J. M. Burns, R. L. Houghton, J. R. David, and S. G. Reed. 1996. rK39: a cloned antigen for *Leishmania chagasi* that predicts active visceral leishmaniasis. J. Infect. Dis. 173:758-761.
4. Beverley S M, Ismach R B, Pratt D M. 1987. Evolution of the genus *Leishmania* as revealed by comparisons of nuclear DNA restriction fragment patterns. Proc Natl Acad Sci USA. 84(2): 484-8.
5. Bora D. 1999. Epidemiology of visceral leishmaniasis in India. Natl Med J India. 12(2): 62-8.
6. Burns J M Jr, Shreffler W G, Benson D R, Ghalib H W, Badaro R, Reed S G. 1993. Molecular characterization of a kinesin-related antigen of *Leishmania chagasi* that detects specific antibody in African and American visceral leishmaniasis. Proc Natl Acad Sci, U S A. 90(2): 775-9.
7. Cupolillo E, Grimaldi G Jr, Momen H. 1994. A general classification of New World *Leishmania* using numerical zymotaxonomy. Am J Trop Med Hyg. 50 (3): 296-311
8. Davidson R N. 1998. Practical guide for the treatment of leishmaniasis. Drugs. 56(6): 1009-18.
9. Desjeux P. 2001. The increase in risk factors for leishmaniasis worldwide. Trans R Soc Trop Med Hyg. 95(3): 239-43.
10. Gari-Toussaint, M., Lelievre, A., Marty, P., Le-Fichoux, Y. 1994. Contribution of serological tests to the diagnosis of visceral leishmaniasis in patients infected with the human immunodeficiency virus. Trans. R. Soc. Trop. Med. Hyg. 88(3): 301-2
11. Ghosh S S, Mukejee S and Adhya S. 1998. Chromosome profile of *Leishmania donovani*: Interstrain and interspecific variations. J. Biosci., 23:3; 247-254.
12. Herwaldt B L. 1999. Leishmaniasis. Lancet. 354(9185): 1191-9.
13. Holmes, D. S and Quigley, M. A. 1981. A rapid boiling method for the preparation of bacterial plasmids. Anal. Biochem. 114, 193-197.
14. Houghton R L, Petrescu M, Benson D R, Skeiky Y A, Scalone A, Badaro R, Reed S G, Gradoni L. 1998. A cloned antigen (recombinant K39) of *Leishmania chagasi* diagnostic for visceral leishmaniasis in human immunodeficiency virus type 1 patients and a prognostic indicator for monitoring patients undergoing drug therapy. J Infect Dis. 177 (5): 1339-44.
15. Jelinek T, Eichenlaub S and Loscher T. 1999. Sensitivity and specificity of a rapid immunochromatographic test for diagnosis of visceral leishmaniasis. Eur. J. Clin. Mirobiol. Infet. Dis. 18: 669-670.
16. Jensen A T, Gasim S, Moller T, Ismail A, Gaafar A, Kemp M, el Hassan A M, Kharazmi A, Alce T M, Smith D F, Theander T G. 1999. Serodiagnosis of *Leishmania donovani* infections: assessment of enzyme-linked immunosorbent assays using recombinant *L. Donovani* gene B protein (GBP) and a peptide sequence of *L. Donovani* GBP. Trans R Soc Trop Med Hyg. 93(2): 157-60.
17. Laemmli, U. K. 1970. Cleavage of structural proteins during the assembly of the head of Bacteriophage T4. Nature. 227, 680-685.
18. Maalej I A, Chenik M, Louzir H, Ben Salah A, Bahloul C, Amri F, Dellagi K. 2003. Comparative evaluation of ELISAs based on ten recombinant or purified *Leishmania* antigens for the serodiagnosis of mediterrean visceral leishmaniasis. Am J Trop Med Hyg; 68(3): 312-20.
19. Manson-Bahr PEC. Diagnosis. 1987. In the Leishmaniases in Biology and Medicine, vol. 2, Clinical Aspects and Control. W Peters & R Killick-Kendrick (eds). New York, Academic Press Inc.: p. 709-729
20. Marfurt J, Niederwieser I, Makia N D, Beck H P, Felger I. 2003. Diagnostic genotyping of Old and New World *Leishmania* species by PCR-RFLP. Diagn Microbiol Infect Dis. 46(2): 115-24.
21. Martin S K, Thuita-Harun L, Adoyo-Adoyo M, Wasunna K M. 1998. A diagnostic ELISA for visceral leishmaniasis, based on antigen from media conditioned by *Leishmania donovani* promastigotes. Ann Trop Med Parasitol. 92(5): 571-7.
22. Mauricio I L, Howard M K, Stothard J R, Miles M A. 1999. Genomic diversity in the *Leishmania donovani* complex. Parasitology. 119 (3): 237-46.

23. Paredes R, Laguna F, Clotet B. 1997. Leishmaniasis in HIV-infected persons: a review. J Int Assoc Physicians AIDS Care. 3 (6): 22-39.
24. Piarroux R, Fontes M, Perasso R, Gambarelli F, Joblet C, Dumon H, Quilici M. 1995. Phylogenetic relationships between Old World *Leishmania* strains revealed by analysis of a repetitive DNA sequence. Mol Biochem Parasitol. 73(1-2): 249-52.
25. Raj V S, Ghosh A, Dole V S, Madhubala R, Myler P J, Stuart K D. 1999. Serodiagnosis of leishmaniasis with recombinant ORFF antigen. Am J Trop Med Hyg. 61(3): 482-7.
26. Rajasekariah G H, Ryan J R, Hillier S R, Yi L P, Stiteler J M, Cui L, Smithyman A M, Martin S K. 2001. Optimisation of an ELISA for the serodiagnosis of visceral leishmaniasis using in vitro derived promastigote antigens. J Immunol Methods. 252(1-2): 105-19.
27. Roberts S C, Swihart K G, Agey M W, Ramamoorthy R, Wilson M E, Donelson J E. 1993. Sequence diversity and organization of the msp gene family encoding gp63 of *Leishmania chagasi*. Mol Biochem Parasitol. 62 (2): 157-71.
28. Samaras N, Spithill T W. 1987. Molecular karyotype of five species of *Leishmania* and analysis of gene locations and chromosomal rearrangements. Mol Biochem Parasitol. 25(3): 279-91.
29. Sambrook. J., Fritsch, E. F. and Maniatis, T. 1989. Molecular cloning, A laboratory Manual. 2 ed. Cold Spring Harbor Laboratory Press, U.S.A.
30. Sanger, F., Nicklen, S. and Coulson, A. R. 1977. DNA sequencing with chain-terminating inhibitors. Proc. Natl. Acad. Sci. U.S.A. 74, 5463-5467.
31. Santos-Gomes G, Gomes-Pereira S, Campino L, Araujo M D, Abranches P. 2000. Performance of immunoblotting in diagnosis of visceral Leishmaniasis in human immunodeficiency virus-*Leishmania* sp.-coinfected patients. J Clin Microbiol. 38(1): 175-8.
32. Sassi A, Louzir H, Ben Salah A, Mokni M, Ben Osman A, Dellagi K. 1999. *Leishmanin* skin test lymphoproliferative responses and cytokine production after symptomatic or asymptomatic *Leishmania major* infection in Tunisia. Clin Exp Immunol. 116(1): 127-32
33. Schallig H D, Schoone G J, Kroon C C, Hailu A, Chappuis F, Veeken H. 2001. Development and application of 'simple' diagnostic tools for visceral leishmaniasis. Med Microbiol Immunol (Berl). 190(1-2):69-71.
34. Schoone G J, Hailu A, Kroon C C, Nieuwenhuys J L, Schallig H D, Oskam L. 2001. A fast agglutination-screening test (FAST) for the detection of anti-*Leishmania* antibodies. Trans R Soc Trop Med Hyg. 95(4), 400-1.
35. Senaldi G, Xiao-su H, Hoessli D. C, Bordier C. 2001. Serological diagnosis of visceral leishmaniasis by a dot-enzyme immunoassay for the detection of a *Leishmania donovani*-related circulating antigen. J Immunol Methods. 193:9-15.
36. Singh S and Sivakumar R. 2003. Recent advances in the diagnosis of leishmaniasis. J. Postgrad. Med. 49(1): 55-60.
37. Singh S, Gilman-Sachs A, Chang K P, Reed S G. 1995. Diagnostic and prognostic value of K39 recombinant antigen in Indian leishmaniasis. J Parasitol. 81 (6): 1000-3.
38. Singh S, Kumari V, Singh N. 2002. Predicting kala-azar disease manifestations in asymptomatic patients with latent *Leishmania donovani* infection by detection of antibody against recombinant K39 antigen. Clin Diagn Lab Immunol. 9 (3): 568-72.
39. Singh S, Mohapatra D P, Sivakumar R. 2000. Successful replacement of foetal calf serum with human urine for in vitro culture of *Leishmania donovani*. J Commun Dis. 32(4): 289-94.
40. Singh S. 1999. Diagnostic and Prognostic markers of anti-kala-azar therapy and vaccination. IN: Proceeding of V Round Table Conference Series. No. 5. Gupta S & Sood OP (Ed). Ranbaxy Science Foundation, New Delhi. pp 95-114.
41. Steinkraus H B, Greer J M, Stephenson D C, Langer P J. 1993. Sequence heterogeneity and polymorphic gene arrangements of the *Leishmania guyanensis* gp63 genes. Mol Biochem Parasitol. 62(2): 173-85.
42. Sundar S, Rai M. 2002. Laboratory diagnosis of visceral leishmaniasis. Clin Diagn Lab Immunol. 9(5): 951-8.
43. Sundar, S, Reed S. G, Singh V. P, Kumar P. C. K and Murray H. W. 1998. Rapid accurate field diagnosis of visceral leishmaniasis. Lancet 351:563-565.
44. The U.S. Pat. No. 5,411,865 by Reed in May 2, 1995
45. The U.S. Pat. No. 5,719,263 by Reed in Feb. 17, 1998
46. The U.S. Pat. No. 6,638,517 by Reed, et al., in Oct. 28, 2003
47. The U.S. Pat. No. 5,912,166 by Reed, et al., in Jun. 15, 1999
48. Towbin, H., Staehlin, T. and Gordan, J. 1976. Electrophoretic transfer of proteins from polyacrylamide gels to nitrocellulose sheets: procedure and some applications. Proc. Natl. Acad. Sci. U.S.A. 76, 4350-4354.
49. Webb J R, Button L L, McMaster W R. 1991. Heterogeneity of the genes encoding the major surface glycoprotein of *Leishmania donovani*. Mol Biochem Parasitol. 48(2): 173-84.
50. WHO expert committee report. Control of the Leishmaniasis. 1991. Technical Report Series 793.
51. Williams, J. E. 1995. *Leishmania* and *Trypanosoma*. In medical parasitology. A practical approach. Gillespie, S. H., Hawkey. P. M., Eds. London, Oxford University Press.
52. Zijlstra E E, Nur Y, Desjeux P, Khalil E A, El-Hassan A M, Groen J. 2001. Diagnosing visceral leishmaniasis with the recombinant K39 strip test: experience from the Sudan. Trop Med Int Health. 6 (2): 108-13.

The invention claimed is:

1. An isolated polypeptide, comprising the amino acid sequence as recited in SEQ ID NO: 5 or SEQ ID NO: 6, wherein said polypeptide has an immunogenic region of a *Leishmania* antigen.

2. The polypeptide as claimed in claim 1, isolated from a strain of *Leishmania donovani*.

3. A method of detecting anti-leishmanial antibodies in a sample, said method comprising:
   binding
   (a) binding anti-leishmanial antibodies from said sample to a polypeptide comprising the amino acid sequence of SEQ ID NO: 5 or SEQ ID NO: 6 that is bound to a solid support or a carrier;
   (b) contacting bound antibodies from step (a) with a secondary antibody or a protein, conjugated to an enzyme or a label and that specifically binds to the bound antibodies of step (a); and
   (c) detecting the anti-leishmanial antibodies in the said sample by detecting the secondary antibody or protein specifically bound to said anti-leishmanial antibodies.

4. The method as claimed in claim 3, wherein the sample is selected from a group consisting of whole blood, serum, plasma and other body fluid.

5. The method as claimed in claim 4, wherein the sample is selected from an animal or a mammal, including human beings.

6. The method as claimed in claim 3, wherein said solid support is selected from a group consisting of nitrocellulose, nylon, latex particles, polypropylene and polystyrene material.

7. The method as claimed in claim 3, wherein said carrier is a gold particle.

8. The method as claimed in claim 3, wherein the anti-human secondary antibody is selected from an antibody classes of IgG, IgM, IgA, IgE and their subclasses.

9. The method as claimed in claim 3, wherein the protein is selected from a group consisting of Protein A and Protein G.

10. The method as claimed in claim 3, wherein the enzyme is selected from the group consisting of Alkaline Phosphatase, Horseradish Peroxidase, β-galactosidase, Urease, Xanthine Oxidase, Glucose Oxidase and penicillinase.

11. The method as claimed in claim 3, wherein said label is selected from a group consisting of enzymes, radioisotopes, biotin, chromophores, fluorophores and chemiluminescent moieties.

12. The method as claimed in claim 3, wherein said detecting step of anti-leishmanial antibodies is selected from the group consisting of detecting fluorescence, detecting chemiluminescence, detecting light absorbance or detecting radio isotopes.

13. A diagnostic kit for detecting anti-leishmanial antibodies comprising a polypeptide as claimed in claim 1, and a secondary antibody or a protein, wherein said secondary antibody or the protein is conjugated to an enzyme or a label, and a reagent for detecting said enzyme or label.

14. The kit as claimed in claim 13, wherein the said polypeptide is bound to a solid support or carrier.

15. The kit as claimed in claim 13, wherein the solid support is selected from the group consisting of nitrocellulose, nylon, latex particles, polypropylene and polystyrene material.

16. The kit as claimed in claim 13, wherein the carrier is a gold particle.

17. The kit as claimed in claim 13, wherein the secondary antibody is selected from an antibody classes of IgG, IgM, IgA, IgE and their subclasses.

18. The kit as claimed in claim 13, wherein the protein is selected from a group consisting of Protein A and Protein G.

19. The kit as claimed in claim 13, wherein said label is selected from a group consisting of an enzyme, a radioisotope, biotin, a chromophore, a fluorophore and a chemiluminescent moiety.

20. The kit as claimed in claim 13, wherein the enzyme is selected from the group consisting of Alkaline Phosphatase, Horseradish Peroxidase, β-galactosidase, Urease, Xanthine Oxidase, Glucose Oxidase and penicillinase.

21. A method of obtaining antibodies to the polypeptide of claim 1, said method comprising injecting said polypeptide into an animal, harvesting the antibodies produced against the polypeptide and purifying said antibodies.

22. The method as claimed in claim 21, wherein the animal is selected from a group consisting of a mouse, a rabbit, a horse, a goat, a sheep, a guinea pig, a pig, a bovine, a rat, a chicken and a hamster.

23. The isolated polypeptide of claim 1 consisting of SEQ ID NO: 5 or SEQ ID NO: 6.

* * * * *